(12) United States Patent
Harada

(10) Patent No.: US 9,901,468 B2
(45) Date of Patent: Feb. 27, 2018

(54) STENT DELIVERY SYSTEM

(75) Inventor: Kinya Harada, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 522 days.

(21) Appl. No.: 13/331,390

(22) Filed: Dec. 20, 2011

(65) Prior Publication Data

US 2012/0116493 A1 May 10, 2012

(30) Foreign Application Priority Data

Aug. 3, 2009 (JP) .................. 2009-180455

(51) Int. Cl.
*A61F 2/06* (2013.01)
*A61F 2/95* (2013.01)
*A61F 2/89* (2013.01)
*A61F 2/966* (2013.01)

(52) U.S. Cl.
CPC ............... *A61F 2/95* (2013.01); *A61F 2/89* (2013.01); *A61F 2002/9517* (2013.01); *A61F 2002/9665* (2013.01)

(58) Field of Classification Search
CPC ...... A61F 2002/9517; A61F 2002/9665; A61F 2/89; A61F 2/95
See application file for complete search history.

(56) References Cited

U.S. PATENT DOCUMENTS

| | | | |
|---|---|---|---|
| 5,201,901 A * | 4/1993 | Harada et al. | 606/198 |
| 5,976,152 A | 11/1999 | Regan et al. | |
| 6,027,508 A * | 2/2000 | Ren et al. | 606/108 |
| 6,435,189 B1 * | 8/2002 | Lewis | A61B 17/22 128/898 |
| 6,709,454 B1 | 3/2004 | Cox et al. | |
| 2010/0076541 A1 | 3/2010 | Kumoyama | |

FOREIGN PATENT DOCUMENTS

| | | |
|---|---|---|
| CN | 2198933 Y | 5/1995 |
| EP | 0 380 668 A1 | 8/1990 |
| JP | 2003-521307 A | 7/2003 |

(Continued)

OTHER PUBLICATIONS

Extended European Search Report dated Nov. 7, 2012, issued by the European Patent Office in the corresponding European Application No. 10806385.0. (6 pages).

(Continued)

*Primary Examiner* — Gregory Anderson
*Assistant Examiner* — Sarah Simpson
(74) *Attorney, Agent, or Firm* — Buchanan Ingersoll & Rooney PC

(57) ABSTRACT

A stent delivery system includes a distal-side tube, a proximal-side tube, a fixing tube, a stent containing tubular member, a stent in the stent containing tubular member, and a pulling wire for moving the stent containing tubular member to the proximal side. The distal-side tube includes a distal-side priming slit provided in a side wall in proximity to a stent proximal end lock section and a proximal-side priming slit provided in a side wall on the proximal side of the distal-side tube. The slits are opened by injecting liquid, with the distal opening or the rear end opening of a guide wire lumen of the distal-side tube closed.

18 Claims, 17 Drawing Sheets

(56) References Cited

FOREIGN PATENT DOCUMENTS

| | | |
|---|---|---|
| JP | 2008-272261 A | 11/2008 |
| JP | 2008-272262 A | 11/2008 |
| WO | 2008/136239 A1 | 11/2008 |
| WO | 2008/136329 A1 | 11/2008 |

OTHER PUBLICATIONS

International Search Report (PCT/ISA/210) dated Nov. 2, 2010, by Japanese Patent Office as the International Searching Authority for International Application No. PCT/JP2010/062810.

Office Action (Notification of First Office Action) dated Nov. 25, 2013, by the State Intellectual Property Office of P. R. China in corresponding Chinese Patent Application No. 201080014121.1, and an English Translation of the Office Action. (21 pages).

Office Action (Notification of the Second Office Action) dated Apr. 15, 2014, by the Chinese Patent Office in corresponding Chinese Patent Application No. 201080014121.1 and an English translation of the Office Action. (13 pages).

\* cited by examiner

STENT DELIVERY SYSTEM

This application is a continuation of International Application No. PCT/JP2010/062810 filed on Jul. 29, 2010, and claims priority to Japanese Application No. 2009-180455 filed on Aug. 3, 2009, the entire content of both of which is incorporated herein by reference.

TECHNICAL FIELD

The present invention relates to a stent delivery system for putting a stent (i.e., indwelling a stent) in a stenosed part or occluded part in a living body such as a blood vessel, bile duct, trachea, esophagus, urethra, digestive tract and other organs.

BACKGROUND DISCUSSION

The have previously been proposed stent delivery systems for putting a stent in a stenosed part or occluded part formed in a living body lumen or body cavity such as a blood vessel, bile duct, esophagus, trachea, urethra, digestive tract and other organs, so as to secure or keep open the lumen or body cavity space.

Stents used with the above-mentioned stent delivery systems are classified into balloon-expandable type stents and self-expandable type stents, according to the function of the stent and the method of indwelling the stent.

The balloon-expandable type stent is a stent which itself does not have an expanding function. In order to put this type of stent in a target part, for example, the stent mounted on a balloon is inserted into the target part, and thereafter the stent is expanded (plastically deformed) by dilating the balloon, whereby the stent is put into firm contact with the inner surface of the target part and fixed there.

Though this type of stent needs the stent-expanding operation as above-mentioned, the stent can be indwelled by mounting the stent directly onto the contracted balloon, so that there is little problem with respect to indwelling the stent.

On the other hand, the self-expandable type stent is a stent which itself has contracting and expanding functions. In order to put this type of stent indwelling in a target part, the stent in contracted state is inserted into the target part, and then the stress loaded on the stent for maintaining the contracted state is removed. For example, the stent is contained in a contracted state in a sheath having an outside diameter smaller than the inside diameter of the target part, the distal end of the sheath is caused to reach the target part, and thereafter the stent is pushed out of the sheath. The stent thus pushed out is released from the sheath, whereby the stress load is removed, so that the stent is allowed to expand to be restored to its pre-contraction shape. This results in the stent being put into firm contact with the inner surface of the target part and fixed there.

Since this type of stent itself has an expanding force, the need for an expanding operation as in the case of a balloon-expandable type stent is absent, so that the stent is free of the problem that its diameter might be gradually decreased by the blood vessel's pressure or the like with the result of restenosis.

However, a self-expandable type stent is generally said to be more difficult than a balloon-expandable type stent to indwell in an accurate manner. The reason is as follows. In the case of a balloon-expandable type stent, after the stent is disposed in a target stenosed part, it is only necessary to inject a fluid into the balloon, so that the stent is typically not moved forward or backward at the time of expansion. On the other hand, the delivery system for a self-expandable type stent is so structured that the stent is contained and restrained between an inner tube and an outer tube, the inner tube is provided on the stent proximal side with an lock section for restricting movement of the stent, and the restraint on the stent is released by pulling the outer tube toward the proximal side, thereby allowing the stent to self-expand. In this case, the stent is liable to move forward at the time of expansion, due to sagging of the outer tube in the body cavity, friction between the outer tube and the body cavity or the catheter in which the outer tube is introduced, or friction between the outer tube and a valve of a device, called introducer, for introducing the system into the living body.

In view of the foregoing, the present applicant has proposed stent delivery systems as shown in Japanese Patent Application Publication No. 2008-272261 (U.S. Patent Application Publication No. 2010/0076541 and European Patent Application Publication No. 2143404) and Japanese Patent Application Publication No. 2008-272262 (U.S. Patent Application Publication No. 2010/0076541, European Patent Application Publication No. 2143404).

The stent delivery system 1 according to Japanese Patent Application Publication No. 2008-272261 includes a distal-side tube 2, a proximal-side tube 4, a slide tube 7 disposed so as to be proximate to the proximal end of a stent containing tubular member 5, a fixing tube 8 to which the distal-side tube 2 and the proximal-side tube 4 are fixed and which can contain the slide tube 7, and pulling wires 6a, 6b for moving the tubular member 5 toward the proximal side.

In addition, the stent delivery system 1 according to the Japanese Patent Application Publication No. 2008-272262 includes a distal-side tube 2, a proximal-side tube 4, a slide tube 7 which is proximate to the proximal end of the stent containing tubular member 5 and which is not fixed to the tubular member 5, a fixing tube 8 to which the distal-side tube 2 and the proximal-side tube 4 are fixed and which can contain the slide tube 7, and a pulling wire 6 for moving the tubular member 5 toward the proximal side. The slide tube 7 can be moved toward the proximal side by pulling of the pulling wire 6, and has a ring-shaped member 75 which is contained therein, to which the pulling wire is fixed, and which can be moved together with the slide tube.

In addition, in this stent delivery system, an opening section for leading out a guide wire inserted via a distal opening of the distal-side tube is provided not at the proximal end of the delivery system but in the fixing tube, so that the operation of exchanging the stent delivery system with another stent delivery system in the process of putting the stent indwelling is easy to carry out. Because the stent can be released by pulling the pulling wire toward the proximal side, positional shifting of the stent at the time of the stent-releasing operation is extremely little. Further, this stent delivery system is advantageous in that unnecessary bending of or damage to a catheter is not generated due to excessive winding-up of the wire for pulling the stent containing tubular member toward the proximal side.

A stent delivery system is inserted into a living body after a priming process for replacement of air in the inside of the system with liquid is carried out. In the stent delivery systems according to the two Japanese application publications mentioned above, the priming process for the spaces formed between the distal-side tube 2 and each of the stent containing tubular member 5, the slide tube 7 and the fixing tube 8 has not necessarily been easy to carry out.

SUMMARY

One aspect of the disclosure here involves a stent delivery system comprising: a distal-side tube possessing a guide wire lumen; a proximal-side tube; a fixing tube fixed to a proximal portion of the distal-side tube and fixed to a distal portion of the proximal-side tube so as not to close a rear end opening of the distal-side tube; a stent containing tubular member enclosing a distal portion of the distal-side tube and slidable toward the proximal end of the distal-side tube; and at least one pulling wire extending inside the proximal-side tube, with the at least one pulling wire having one end section fixed to the stent containing tubular member so that a proximal direction pulling force applied to the at least one pulling wire moves the stent containing tubular member in the proximal direction toward the proximal-side tube. A cylindrically-shaped stent is located in the stent containing tubular member in a compressed state in which the stent is compressed inwardly toward a central axis of the stent, with the stent being expandable outwardly when released to outside the stent containing tubular member. A stent proximal end lock section is located on the distal side of the distal-side tube and abuts on the proximal end of the stent contained in the stent containing tubular member to restrict movement of the stent in the proximal direction. At least one distal-side priming slit passes through a side wall of the distal-side tube in proximity to the stent proximal end lock section, and at least one proximal-side priming slit passes through the side wall of the distal-side tube on a proximal side of the distal-side tube. The at least one distal-side priming slit and the at least one proximal-side priming slit are opened by injecting liquid into the guide wire lumen, with a distal opening or a rear end opening of the guide wire lumen closed.

The stent delivery system is constructed in such a way that a priming process to be conducted before use of the system is rather easy to carry out and the operation of indwelling the stent or putting it in place can be carried out relatively easily and assuredly.

By injecting a liquid (priming solution) into the guide wire lumen in the condition where the distal opening or the rear end opening of the guide wire lumen is sealed or closed, a priming process for the space formed in the inside of the distal-side tube and on the outside of the distal-side tube, in the stent delivery system, can be carried out rather easily. Further, the distal-side priming slit and the proximal-side priming slit are opened by injecting a liquid into the guide wire lumen in the condition where the distal opening or the rear end opening of the guide wire lumen is closed or sealed. The distal-side priming slit and the proximal-side priming slit are normally in a closed state, so that there is little possibility of kinking which might arise from the priming opening sections, and it is possible to restrain the flow of blood arising from the priming opening sections at the time of indwelling the stent or putting the stent in a living body.

The distal-side priming slit and/or the proximal-side priming slit can be provided plural in number and axially spaced apart from one another. A slit adhesion inhibitive material can be deposited on the internal surface of the distal-side priming slit and/or the proximal-side priming slit. The external surface of the distal-side tube and/or an internal surface of the stent can also be coated with a material that facilitates or improves sliding.

With plural distal-side priming slits, at least one of the distal-side priming slits is provided in a side wall on the proximal side relative to the stent proximal end lock section. The distal-side priming slit and/or the proximal-side priming slit can be arranged parallel to the center axis of the distal-side tube.

The distal-side tube can include a reinforcement layer provided over the whole or a part thereof, and the distal-side priming slit and/or the proximal-side priming slit can be provided in the part where the reinforcement layer is formed.

The stent delivery system can also be outfitted with a slide tube disposed proximate to the proximal end of the stent containing tubular member. The fixing tube can contain the slide tube from the proximal side or the slide tube can be fitted over the fixing tube from the proximal side. The slide tube is preferably movable toward the proximal side together with the stent containing tubular member by pulling of the pulling wire and is not fixed to the stent containing tubular member.

The slide tube preferably includes a slide tube body and a distal-side tubular member which is fixed to a distal portion of the slide tube body. The distal-side tubular member covers the distal end of the slide tube body and extends toward the distal-side of the stent delivery system beyond the distal end of the slide tube body. The distal-side tubular member is an integrally formed tubular body having a reduced diameter section which is located between the distal end and the proximal end of the distal-side tubular member and which is reduced at least in inside diameter.

The stent delivery system can also include a ring-shaped member contained between the distal end of the slide tube body and the reduced diameter section of the distal-side tubular member, with the pulling wire fixed to the ring-shaped member. The ring-shaped member is not fixed to either the slide tube body or the distal-side tubular member, and is turnably contained between the distal end of the slide tube body and the reduced diameter section of the distal-side tubular member. The stent delivery system includes an operating section having a pulling wire winding-up mechanism for winding up the pulling wire so as to move the stent containing tubular member toward the proximal side. The operating section is provided at the proximal portion of the proximal-side tube.

According to another aspect, a stent delivery system comprises: a distal-side tube possessing a guide wire lumen to receive a guide wire, with the guide wire lumen being surrounded by a side wall of the distal-side tube, and the guide wire lumen extending from an open distal end to an open proximal end so that a guide wire received in the guide wire lumen passes through the open distal end of the guide wire lumen and passes through the open proximal end of the guide wire lumen; a proximal-side tube; a fixing tube positioned axially between the distal-side tube and the proximal-side tube; a stent containing tubular member, with a distal portion of the distal-side tube passing through the stent containing tubular member so that the distal-side tube and the stent containing tubular member axially overlap one another with an annular space between an inner surface of the stent containing tubular member and an outer surface of the distal-side tube, and with the stent containing tubular member being axially movable in a proximal direction relative to the distal-side tube; at least one pulling wire positioned in the proximal-side tube and possessing an end fixed to the stent containing tubular member so that a pulling force applied to the at least one pulling wire in the proximal direction moves the stent containing tubular member in the proximal direction; and a cylindrically-shaped stent located in the annular space between the inner surface of the stent containing tubular member and the outer surface of the distal-side tube, with the stent being compressed inwardly while in the annular space and being automatically expandable outwardly when released to outside the annular space. A stent proximal end lock section is fixed to the distal-side tube, with the stent proximal end lock section being positioned axially between a proximal end of the stent and a proximal-most end of the stent containing tubular member to restrict movement of the stent in the proximal direction. At least one priming slit passes through the side wall of the distal-side tube and is configured to be opened upon injecting liquid into the guide wire lumen while the open distal end or the open proximal end is closed, with the at least one priming slit being positioned between a proximal end of the stent containing tubular member and a distal end of the stent containing tubular member. The at least one priming slit passes through the side wall of the distal-side tube at a location between the distal end of the stent containing tubular member and the proximal end of the stent containing tubular member.

Another aspect involves a method of priming a stent delivery system. The method comprises sealing an open end of a guide wire lumen in a distal-side tube of the stent delivery system, wherein the stent delivery system also includes: a proximal-side tube; a fixing tube positioned axially between the distal-side tube and the proximal-side tube; a stent containing tubular member through which extends a distal portion of the distal-side tube; at least one pulling wire positioned in the proximal-side tube and possessing an end fixed to the stent containing tubular member to move the stent containing tubular member in a proximal direction by applying a pulling force to the at least one pulling wire in the proximal direction; a cylindrically-shaped stent located in the stent containing tubular member in an axially inwardly compressed state, with the stent being automatically expandable outwardly when released to outside the stent containing tubular member; a stent proximal end lock section fixed to the distal-side tube at a position axially between a proximal-most end of the stent and a proximal-most end of the stent containing tubular member to restrict movement of the stent in the proximal direction; and at least one priming slit passing through a side wall of the distal-side tube at a location between a proximal end of the stent containing tubular member and a distal end of the stent containing tubular member. The method further involves introducing priming solution into the guide wire lumen while the one end of the guide wire is closed, with the introduction of the priming solution into the guide wire lumen opening the at least one priming slit so that the priming solution flows through the priming slit such that the priming solution flowing through the at least one priming slit contacts an outer surface of the distal-side tube.

DETAILED DESCRIPTION

Figure 1:
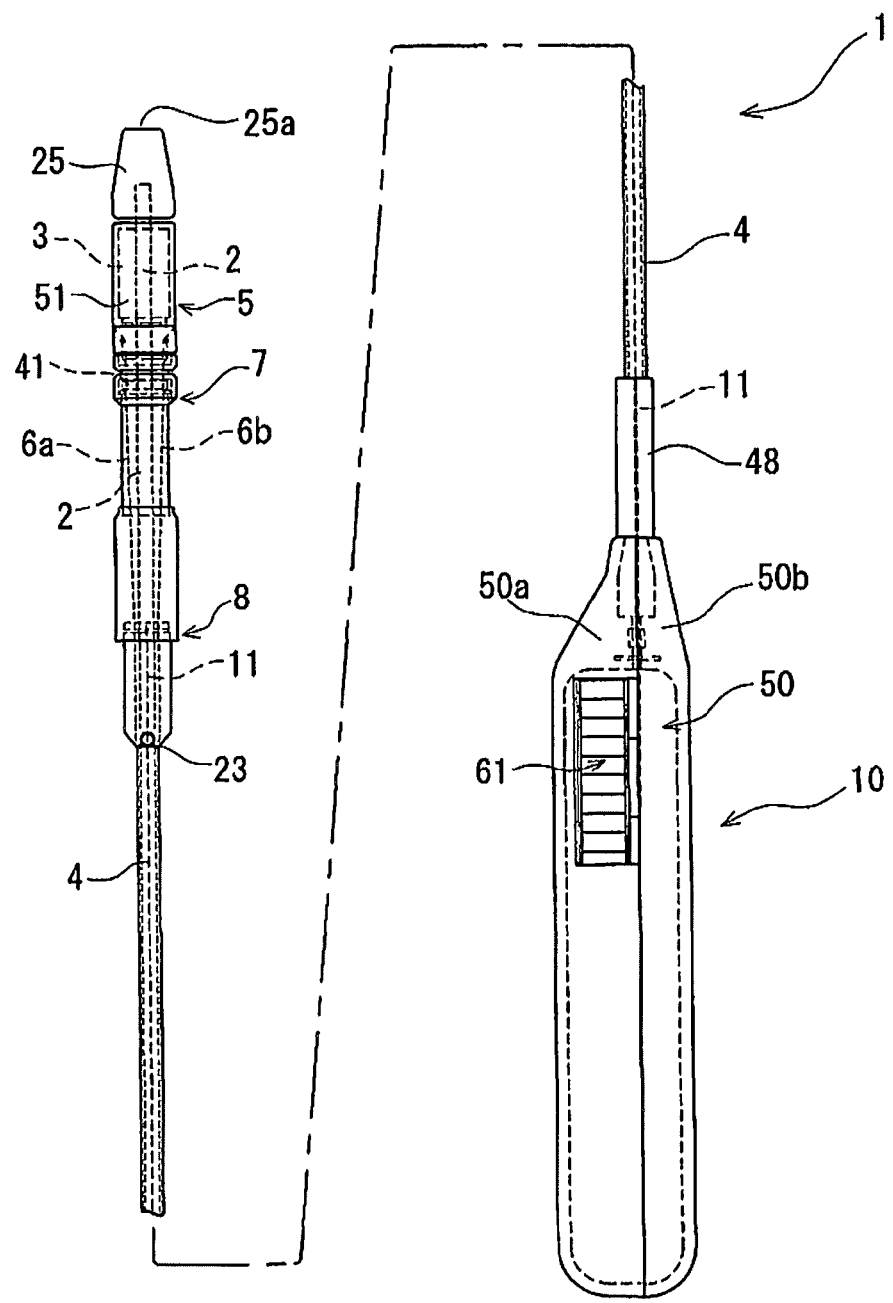
FIG. 1 is an exploded side view of a stent delivery system according to one embodiment disclosed by way of example.

Set forth below is a detailed description of the stent delivery system (living organ dilating instrument) disclosed here referring to several embodiments described by way of example.

The stent delivery system 1 shown in FIGS. 1-11 includes a distal-side tube 2 having a guide wire lumen 21, a proximal-side tube 4, a fixing tube 8 to which a proximal portion of the distal-side tube 2 and a distal portion of the proximal-side tube 4 are fixed so as not to close a rear end opening of the distal-side tube 2, a stent containing tubular member 5 which encloses the distal side of the distal-side tube 2 and which can be slid toward the proximal end of the distal-side tube 2, a stent 3 contained in the stent containing tubular member 5, and pulling wires 6 (6a, 6b) which each have one end section fixed to the stent containing tubular member 5, which extend inside the proximal-side tube 4 and which serve for moving the stent containing tubular member 5 toward the proximal side by pulling the pulling wires 6 toward the proximal end of the proximal-side tube.

The stent 3 possesses a substantially cylindrical shape, is contained in the stent containing tubular member 5 while compressed toward the center axis of the stent, and is restored to its pre-compression shape through outward expansion when released from the stent containing tubular member 5.

In addition, the distal-side tube 2 includes: a stent proximal end lock section 22 which is located on the distal side of the distal-side tube 2 and which abuts on the proximal end of the stent 3 contained in the stent containing tubular member 5 so as to restrict movement of the stent 3 toward the proximal side; distal-side priming slits 45 provided in a side wall in proximity to the stent proximal end lock section 22; and proximal-side priming slits 46 provided in a side wall on the proximal side of the distal-side tube 2. The distal-side priming slits 45 are positioned between the proximal end of the stent containing tubular member 5 and the distal end of the stent containing tubular member 5. In the illustrated embodiment, the axial distance between the proximal-most distal-side priming slit 45 and the distal-most proximal-side priming slits 46 is greater than the distance between axially adjacent distal-side priming slits 45 and is also greater than the distance between axially adjacent proximal-side priming slits 46. The distal-side priming slits 45 and the proximal-side priming slits 46 are opened by injecting a liquid into the guide wire lumen 21 in the condition where a distal opening 25a or a rear end opening 23 of the guide wire lumen 21 is closed.

In addition, in the stent delivery system 1 according to this embodiment, the outside diameter of the proximal-side tube 4 is smaller than the outside diameter of a maximum diameter section on the distal side relative to the proximal-side tube 4 of the stent delivery system 1. This ensures that, even in the condition where the guide wire extending to the proximal side relative to the opening 23 is set along a side surface of the proximal-side tube, the outside diameter of the proximal-side tube can be made comparable to the outside diameter of the maximum diameter section on the distal side relative to the proximal-side tube of the stent delivery system, so that the stent delivery system can be inserted into a blood vessel having a relatively small diameter.

The stent delivery system 1 according to this embodiment is provided, at a proximal portion of the proximal-side tube 4, with a pulling wire winding-up mechanism for winding up the pulling wires 6 so as to move the stent containing tubular member 5 toward the proximal side or in the proximal direction.

The stent delivery system 1 according to this embodiment includes the distal-side tube 2, the stent 3, the proximal-side tube 4, the stent containing tubular member 5, the pulling wires 6, a slide tube 7, the fixing tube 8, and an operating section 10 having the winding-up mechanism for the pulling wires 6. In addition, the fixing tube 8 interconnects the distal-side tube 2 and the proximal-side tube 4, and has the opening 23 which communicates with a proximal portion of the distal-side tube 2.

Figure 2:
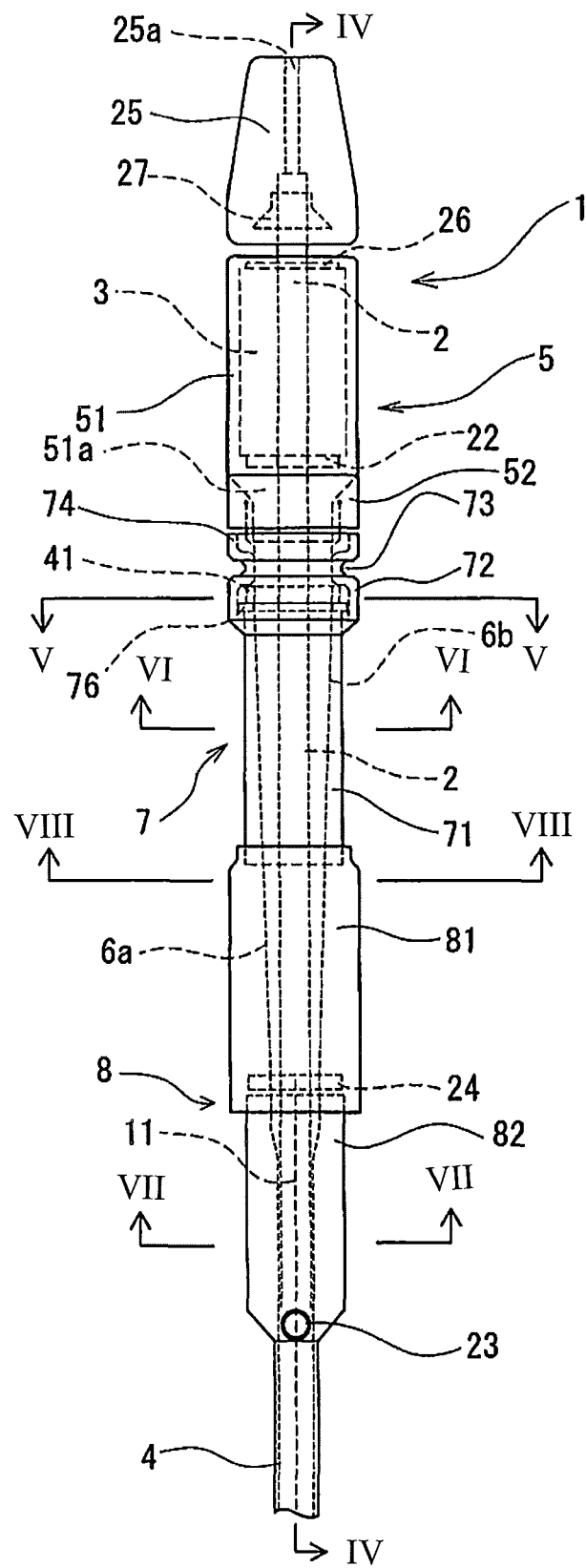
FIG. 2 is an enlarged side view of a distal portion of the stent delivery system of FIG. 1.
Figure 3:
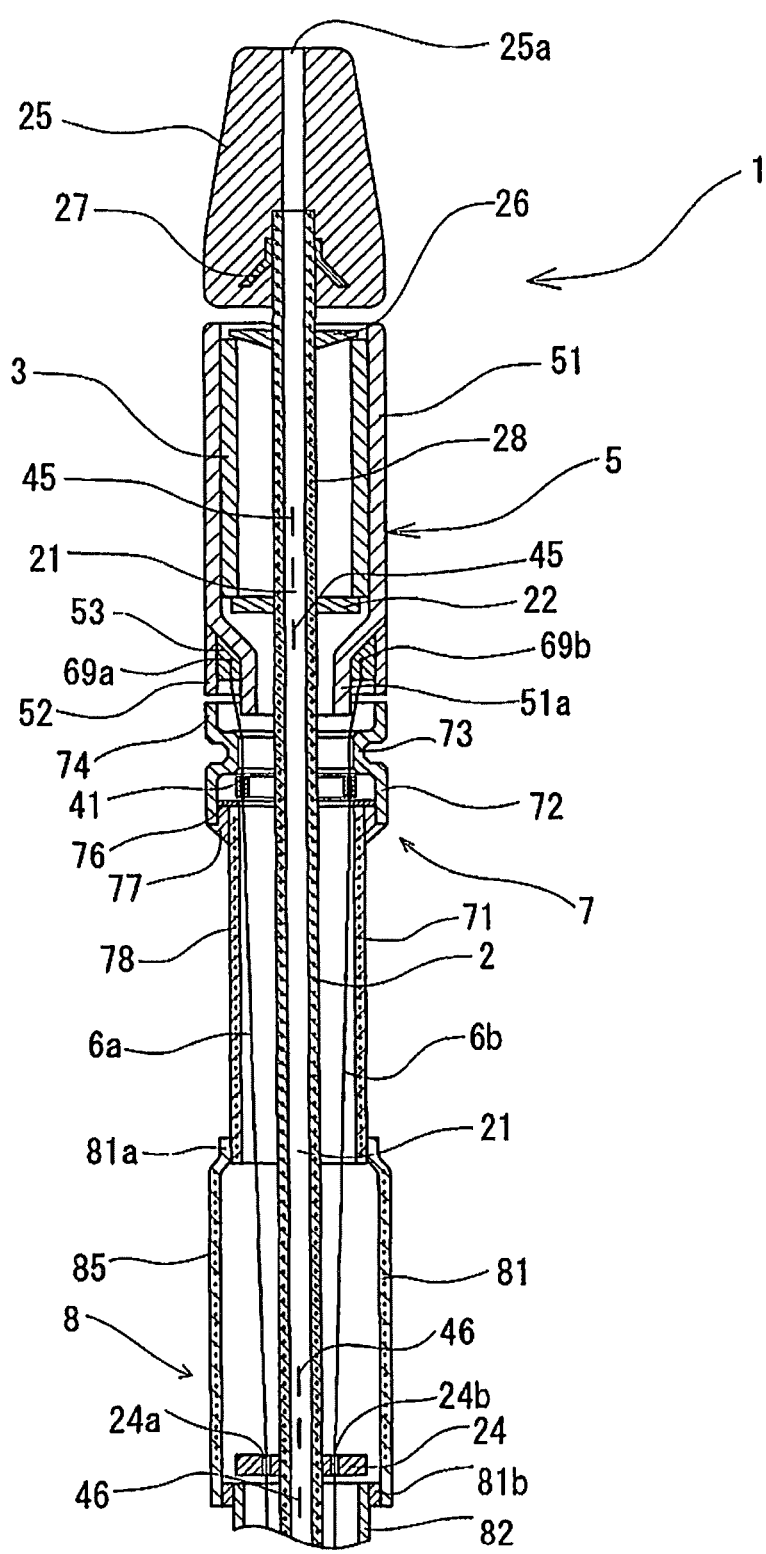
FIG. 3 is an enlarged longitudinal cross-sectional view of the distal portion of the stent delivery system of FIG. 1.
Figure 4:
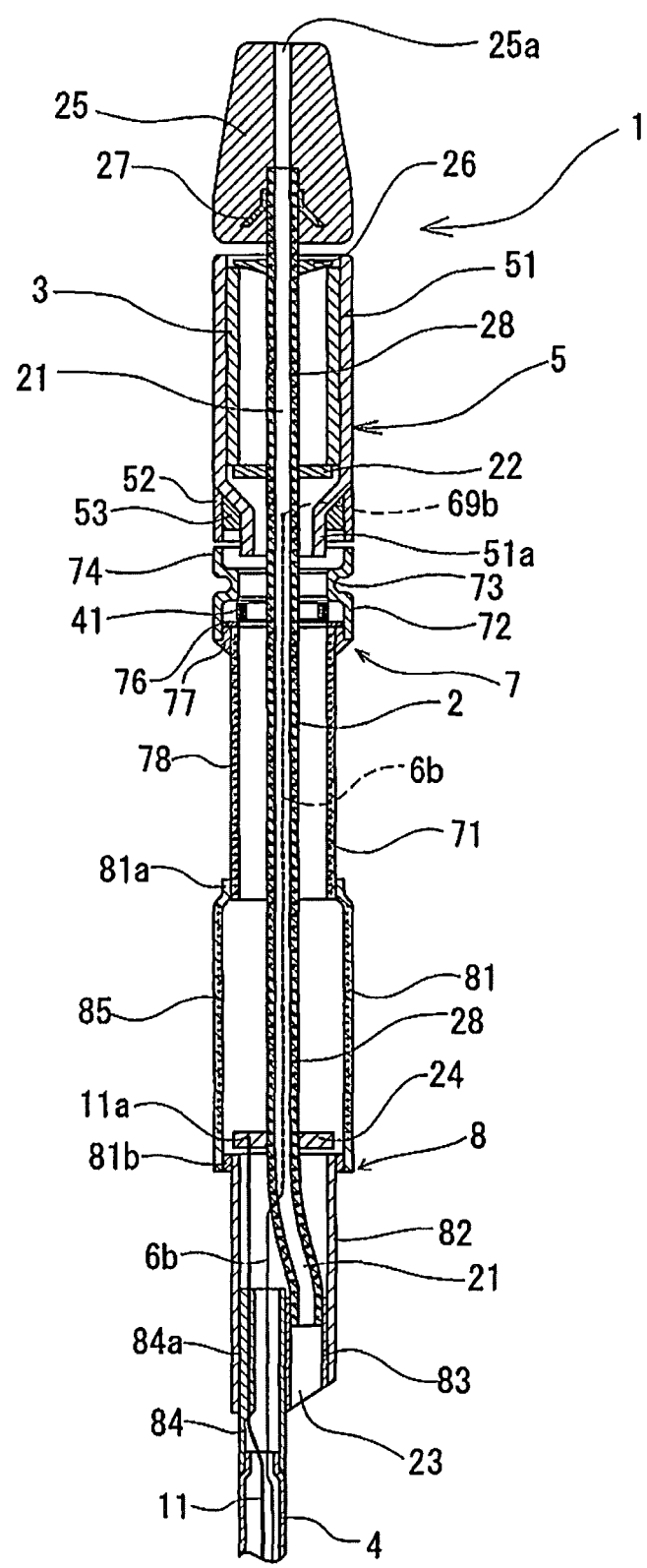
FIG. 4 is a cross-sectional view taken along the section line IV-IV in FIG. 2

As shown in FIGS. 1 to 10, the distal-side tube 2 is a tube body having the guide wire lumen 21 penetrating therethrough from the distal end of the distal-side tube 2 to the proximal end of the distal-side tube 2. The distal portion of the distal-side tube 2 is formed by a distal end member 25 fixed to its distal end, and a distal opening 25a is provided at the distal end of the distal end member 25. The distal opening 25a communicates with the lumen 21 in the distal-side tube 2. The distal end member 25 may be formed integrally with the distal-side tube 2. In addition, the distal-side tube 2 is fixed to the fixing tube 8 at a proximal portion thereof. The proximal end of the distal-side tube 2 communicates with the opening 23 formed in the fixing tube 8. In addition, a proximal portion of the distal-side tube 2 is bent or curved as shown in FIG. 4. As shown in FIGS. 1 and 4, the opening 23 is formed obliquely so as to be inclined toward the proximal side. This facilitates guiding of a guide wire.

As shown in the figures, the distal-side tube 2 is a tube body having the guide wire lumen 21 penetrating therethrough from the distal end to the proximal end of the tube body (distal-side tube 2). The outside diameter of the distal-side tube 2 is 0.3 to 2.0 mm, preferably 0.5 to 1.5 mm, the inside diameter of the distal-side tube 2 is 0.2 to 1.5 mm, preferably 0.3 to 1.2 mm, and the length of the distal-side tube 2 is 20 to 600 mm, preferably 30 to 500 mm.

In addition, the distal end member 25 is located on the distal side relative to the distal end of the stent containing tubular member 5, and, as shown in FIGS. 1 to 4, it preferably possesses a tapered shape such as to gradually decrease in diameter toward the distal end. Such a shape facilitates insertion of the stent delivery system 1 into a stenosed part. In addition, the distal-side tube 2 is preferably provided with a stopper which is provided on the distal side relative to the stent 3 and which inhibits the stent containing tubular member from moving toward the distal side. In this embodiment, the proximal end of the distal end member 25 can abut on the distal end of the stent containing tubular member 5, and functions as the above-mentioned stopper.

The outside diameter of a distal-most portion of the distal end member (distal portion) 25 is preferably 0.5 to 1.8 mm. In addition, the outside diameter of a maximum diameter section of the distal end member (distal portion) 25 is preferably 0.8 to 4.0 mm. Furthermore, the length of the distal-side tapered section is preferably 2.0 to 20.0 mm.

As shown in FIGS. 3 and 4, the distal-side tube 2 has the stent proximal end lock section 22 provided at a position deviated by (spaced) a predetermined distance to the proximal side from the distal end of the tube 2, for restricting movement of the stent 3 toward the proximal side. As illustrated, the stent proximal end lock section 22 is also positioned axially between the proximal-most end of the stent 3 and the proximal-most end of the stent containing tubular member 5. The lock section 22 is preferably an annular projected section. In addition, the distal side relative to the stent proximal end lock section 22 serves as a stent containing part. The outside diameter of the lock section 22 is so set that the lock section 22 abuts on the proximal end of the stent 3 in a compressed state. Even when the stent containing tubular member 5 is moved toward the proximal side, the stent 3 is kept in position by the lock section 22; as a result, therefore, the stent 3 is released from the stent containing tubular member 5.

In the stent delivery system 1 according to this embodiment, as shown in FIGS. 3 and 4, the distal-side tube 2 has a stent distal end lock section 26 provided at a position deviated by, or spaced, a predetermined length (roughly equal to the axial length of the stent) toward the distal side from the stent proximal end lock section 22. As shown in FIGS. 3 and 4, the stent distal end lock section 26 is located slightly on the proximal side relative to the distal end of the stent containing tubular member 5. The lock section 26 is preferably an annular projected section. The space between the stent distal end lock section 26 and the stent proximal end lock section 22 serves as a stent containing part. The outside diameter of the lock section 26 is so set that the lock section 26 can abut on the distal end of the stent 3 in a compressed state. In addition, the proximal end surface of the stent distal end lock section 26 is a tapered surface such as to decrease in diameter toward the proximal side. This helps ensure that the stent distal end lock section 26 is not an obstacle at the time of release of the stent, and recovery of the stent delivery system 1 after the release of the stent 3 (specifically, containment of the stent delivery system into a guiding sheath or a sheath) is facilitated.

The outside diameters of the stent proximal end lock section 22 and the stent distal end lock section 26 are preferably 0.5 to 4.0 mm. While the stent proximal end lock section 22 and the stent distal end lock section 26 are preferably annular projected sections as shown in the figures, the lock sections are not limited in that regard so long as they are configured to restrict movement of the stent 3 and permit the stent 3 to be pushed out. For instance, each of the stent proximal end lock section 22 and the stent distal end lock section 26 may be one or a plurality of projections provided integrally with or separately from the distal-side tube 2. In addition, the stent proximal end lock section 22 and the stent distal end lock section 26 may be composed of separate members formed from a radiopaque material. This helps ensures that the position of the stent can be accurately grasped under radioscopy, so that procedure is facilitated. Preferable examples of the radiopaque material include gold, platinum, platinum-iridium alloy, silver, stainless steel, and their alloys. The projected sections are mounted in position by a method in which a wire formed from the radiopaque material is wound around the outer surface of the distal-side tube, or a method in which a pipe formed from the radiopaque material is caulked onto or adhered to the distal-side tube.

The distal-side tube 2 has the distal-side priming slits 45 provided in the side wall in proximity to the stent proximal end lock section 22. Especially, in the stent delivery system 1 according to this embodiment, a plurality of the distal-side priming slits 45 are provided along the axial direction of the distal-side tube 2. The number of slits 45 is preferably about two to five. The distal-side priming slits 45 are so formed as to extend along the axial direction of the distal-side tube 2. Particularly, the distal-side priming slits 45 are preferably so formed as to be parallel to a center axis of the distal-side tube 2. In addition, the distal-side priming slits 45 are preferably provided in the side wall on the distal side and the proximal side, relative to the stent proximal end lock section 22. That is, the distal-side priming slits 45 extend on the distal side of the stent proximal end lock section 22 and also extend on the proximal side of the stent proximal end lock section 22. In the stent delivery system 1 according to this embodiment, a plurality (specifically two in the illustrated embodiment) of slits 45 is provided in the side wall on the distal side relative to the stent proximal end lock section 22, and one or more of the slit(s) 45 is provided also in the side wall on the proximal side relative to the stent proximal end lock section 22.

The distal-side tube 2 has the proximal-side priming slits 46 provided in the side wall on the proximal side of the distal-side tube 2. In the stent delivery system 1 according to this embodiment, a plurality of the proximal-side priming slits 46 are provided along the axial direction of the distal-side tube 2. The number of slits 46 is preferably about two to five. In addition, the proximal-side priming slits 46 are so formed as to extend along the axial direction of the distal-side tube 2. Particularly, the proximal-side priming slits 46 are preferably arranged parallel to the center axis of the distal-side tube 2.

On the outer surface of the distal-side tube 2, a slide tube lock section 24 is provided in the fixing tube 8, specifically, at a position corresponding to a proximal portion of a distal-side fixing tube 81, as shown in FIG. 3. In addition, the proximal-side priming slits 46 are formed in a side wall in proximity to the slide tube lock section 24. That is, in the stent delivery system 1 according to this embodiment, a plurality (specifically, two) of the slits 46 are provided in the side wall on the distal side relative to the slide tube lock section 24, and one or more of the slit(s) 46 are provided also on the proximal side relative to the slide tube lock section 24.

The distal-side priming slits 45 and the proximal-side priming slits 46 are not opened in the normal state. The slits 45 and 46 are so-called cuts which have no width. This helps ensure that the slits 45 and 46 are so formed as to be opened by injecting a liquid into the guide wire lumen 21 in the condition where the distal opening 25a or the rear end opening 23 of the guide wire lumen 21 is closed. In addition, the slits 45 and 46 are so formed as not to substantially permit passage of a liquid therethrough, even when a liquid is injected into the guide wire lumen 21 in the condition where the distal opening 25a or the rear end opening 23 is not closed.

The length of the distal-side priming slit 45, which varies depending on the number of the slits provided, is preferably 0.5 to 5 mm, particularly preferably 1 to 3 mm.

The distal-side priming slits 45 and the proximal-side priming slits 46 can be relatively easily formed, without using an exclusive-use processing equipment or an eximer laser apparatus or the like. In addition, the slits 45 and 46 are relatively thin cuts, so that the inner tube portions where the slits are formed would be less liable to kink even when the inner tube is bent.

The slits 45 and 46 can be formed, for example, by a method in which a core metal is inserted into the distal-side tube, a slit-forming mask provided with a slit-forming window section is set, a cutter is inserted into the window section, and the cutter is moved in the manner of drawing a line.

In the stent delivery system 1 disclosed here, both the distal-side priming slits 45 and the proximal-side priming slits 46 are provided, so that the liquid flows from both slits at the time of priming, and, accordingly, priming can be performed at a relatively low pressure, smoothly and in a fairly short time.

The material for forming the distal-side tube is preferably a material which has hardness and flexibility. Examples of the suitably usable material include polyolefins such as polyethylene, polypropylene, etc., polyamides, polyesters such as polyethylene terephthalate, etc., fluoro-polymers such as ETFE, etc., PEEK (polyether ether ketone), and polyimides. Among these resins, particularly preferred are thermoplastic resins. The outer surface of the distal-side tube which is exposed may be coated with a biocompatible material, especially, an antithrombotic material. Examples of the antithrombotic material which can be suitably used here include polyhydroxyethyl methacrylate, and hydroxyethyl methacrylate-styrene copolymers (e.g., HEMA-St-HEMA block copolymer).

In the case where the distal portion is composed of a member separate from the distal-side tube, the distal portion (distal end member) 25 is preferably formed from a flexible material. Examples of the flexible material include synthetic resin elastomers such as olefin elastomers (e.g., polyethylene elastomer, polypropylene elastomer), polyamide elastomers, styrene elastomers (e.g., styrene-butadiene-styrene copolymer, styrene-isoprene-styrene copolymer, styrene-ethylenebutylene-styrene copolymer), polyurethane, urethane elastomers, fluoro-resin elastomers, etc., and rubbers such as synthetic rubbers such as urethane rubber, silicone rubber, etc. and natural rubbers such as latex rubber, etc.

Further, the distal-side tube 2 may have a reinforcement layer 28 provided over the whole or at a part of the distal-side tube 2. Furthermore, the distal-side priming slits 45 and/or the proximal-side priming slits 46 may be provided at a part where the reinforcement layer 28 is provided. In addition, the reinforcement layer 28 may be provided at a part exclusive of the slit formation parts of the distal-side tube 2. And distal-side tube can be configured so that it does not include such a reinforcement layer. The reinforcement layer is preferably a network-like reinforcement layer. The network-like reinforcement layer is preferably formed of braid wires. The braid wire is, for example, a wire braid, which can be formed from wire of a metal such as stainless steel, an elastic metal, a superelastic alloy, or a shape memory alloy having a wire diameter of 0.01 to 0.3 mm, preferably 0.03 to 0.2 mm. Or, alternatively, the braid wire may be formed from synthetic fiber such as polyamide fibers, polyester fibers, polypropylene fibers, etc.

An outer surface of the distal-side tube 2 and/or an inner surface of the stent 3 is preferably coated with a material that facilitates or improves sliding. In addition, it is more preferable that an inner surface of the distal-side tube 2, an inner surface of the stent containing tubular member 5, an inner surface of the slide tube body 71, an inner surface of the fixing tube 81, and an inner surface of a ring-shaped member 41 are also coated with a material that facilitates or improves sliding. The surface to be coated with the material is preferably the entire surface, but the surface may be only partly coated. This helps ensure improved movement of the stent containing tubular member 5 and the ring-shaped member 41. In addition, sliding of a guide wire is also improved.

The material that facilitates or improves sliding is preferably silicone oil or a silicone resin. As the silicone oil, there is preferably used one which conforms to the silicone oil standard (II: Notification by the Medical Devices Division, the Pharmaceutical Affairs Bureau, Ministry of Health and Welfare, Japan, No. 327) or a foreign country standard equivalent thereto. As the silicone resin, there is preferably used a solidified product of a silicone solution containing dimethylpolysiloxane or the like as a main ingredient.

In addition, a slit adhesion inhibitive material is preferably deposited on the inner surfaces of the distal-side priming slits 45 and the proximal-side priming slits 46. With the slit adhesion inhibitive material thus deposited, opening of the slits at the time of priming is facilitated. As the slit adhesion inhibitive material, the materials mentioned above as examples of the material that facilitates or improves sliding can be suitably used.

The application of the material (material that facilitates or improves sliding) to the outer surface of the distal-side tube 2, the inner surface of the distal-side tube 2, the inner surface of the stent 3, the inner surface of the stent containing tubular member 5, the inner surface of the slide tube body 71, the inner surface of the fixing tube 81, and the inner surface of the ring-shaped member 41 can be carried out by a process similar to the priming (described later) conducted using the distal-side priming slits and the proximal-side priming slits. Specifically, a cap member 47 is attached to the distal end member 25 so that the distal opening 25*a* is thereby closed. Then, in this condition, a syringe (not shown) filled with a material-containing liquid (for example, a liquid silicone) is attached to the opening 23 of the fixing tube 8, and a plunger of the syringe is pushed, thereby injecting the material-containing liquid into the distal-side tube 2. By the injection of the material-containing liquid, the distal-side priming slits 45 and the proximal-side priming slits 46 are opened, and the material-containing liquid flows into the space formed in the inside of the distal-side tube and on the outside of the distal-side tube, in the stent delivery system. Then, an excessive quantity of the material-containing liquid is removed. By such a process, the desired coating of the surfaces with the material can be achieved. In addition, deposition of the slit adhesion inhibitive material to the inner surfaces of the distal-side priming slits 45 and the proximal-side priming slits 46 can also be carried out by a process equivalent to the above-mentioned process. Especially, in the case where the same material as the material that facilitates or improves sliding is used as the slit adhesion inhibitive material, the deposition of the slit adhesion inhibitive material can be carried out simultaneously by the above-mentioned injection of the material-containing liquid into the distal-side tube 2: The above-mentioned process may be conducted by sealing the opening 23 of the fixing tube 8 with a seal member or the like and attaching a syringe filled with the material-containing liquid to the distal end member 25.

In addition, in the stent delivery system 1 according to this embodiment, the distal-side tube 2 and the distal end member 25 are formed as separate members, and a stopper member 27 is fixed to a distal portion of the distal-side tube 2. The stopper member 27 has a tubular section fixed to the distal-side tube 2, and a skirt section spreading in a tapered form from the tubular section. The stopper member 27 is embedded in the distal end member 25, thereby preventing the distal end member 25 from slipping off or moving toward the distal side. The stopper member 27 is preferably formed from a metal (for example, stainless steel).

As shown in FIGS. 1, 2 and 4, the proximal-side tube 4 is a tube body penetrating therethrough from the distal end to the proximal end thereof, and has the operating section 10 fixed to the proximal end of the proximal-side tube 4. A distal portion of the proximal-side tube 4 is joined to the fixing tube 8 by a fixing member 84. The proximal-side tube 4 is provided therein with a pulling wire lumen in which the pulling wire 6 can be passed.

The proximal-side tube 4 has a length of 300 to 1500 mm, more preferably 700 to 1400 mm, an outside diameter of 0.5 to 1.5 mm, preferably 0.6 to 1.3 mm, and an inside diameter of 0.3 to 1.4 mm, preferably 0.5 to 1.2 mm.

The distance of offset between the center axis of the proximal-side tube 4 and the center axis of the distal-side tube 2 is preferably 0.2 to 2.0 mm, particularly preferably 0.5 to 1.5 mm.

The material for forming the proximal-side tube 4 is preferably a material which has hardness and flexibility. Examples of the suitably usable material include polyolefins such as polyethylene, polypropylene, etc., nylon, polyethylene terephthalate, fluoro-polymers such as ETFE, etc., PEEK (polyether ether ketone), and polyimides. Incidentally, an outer surface of the proximal-side tube may be coated with a biocompatible material, particularly, an antithrombotic material. Examples of the antithrombotic material which can be used here include polyhydroxyethyl methacrylate, and hydroxyethyl methacrylate-styrene copolymers (e.g., HEMA-St-HEMA block copolymer). In addition, a material comparatively high in rigidity may also be used as the material for forming the proximal-side tube 4. Examples of such comparatively rigid material include metals such as Ni—Ti alloy, brass, stainless steel, aluminum, etc., and resins comparatively high in rigidity, such as polyvinyl chloride, polycarbonate, etc.

Figure 11:
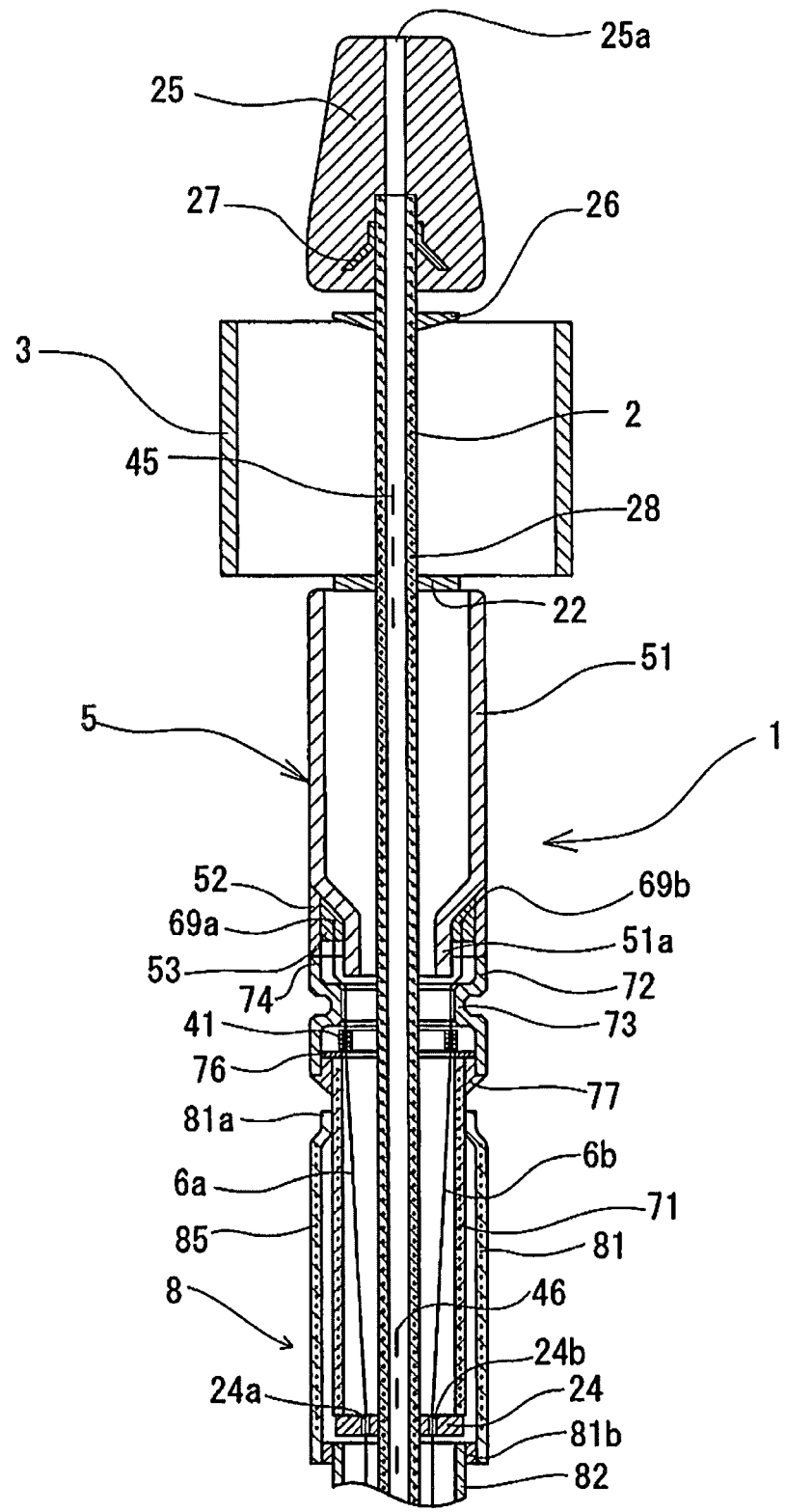
FIG. 11 is an enlarged cross-sectional view of a part of the stent delivery system illustrating operation of the stent delivery system.

As shown in FIGS. 1 to 4 and 9, the stent containing tubular member 5 is a tubular body having a predetermined length, and is opened at its distal or front end and at its proximal or rear end. The distal opening functions as a release port for the stent 3 at the time of putting the stent 3 indwelling in a stenosed part in a body cavity. As shown in FIG. 11, by being pushed out via the distal opening, the stent 3 is relieved from a stress load and expands, to be restored to its pre-compression shape.

The length of the stent containing tubular member 5 is preferably about 20 to 400 mm, particularly preferably 30 to 300 mm. In addition, its outside diameter is preferably about 0.8 to 4.0 mm, particularly preferably 1.5 to 3.0 mm. Besides, the inside diameter of the stent containing tubular member 5 is preferably about 1.0 to 2.5 mm.

The stent containing tubular member 5 includes a tubular member body section 51 having an axially extending small diameter section 51*a* provided at a proximal portion of the tubular member 5, and an axially extending tubular section 52 enclosing or surrounding the small diameter section 51*a*. A proximal portion of the small diameter section 51*a* axially protrudes or projects beyond the proximal end of the tubular section 52. Specifically, distal portions 69 (69*a*, 69*b*) of the pulling wires 6 (6*a*, 6*b*) enter into a gap between the small diameter section 51*a* and the tubular section 52, and are fixed to the stent containing tubular member 5 by a fixing agent 53 filling the gap. The small diameter section 51*a* has a tapered portion decreasing in outside diameter toward the proximal side, and a short cylindrical portion extending toward the proximal side relative to the tapered portion. In addition, the tubular section 52 is fixed to a proximal portion of the tubular member body section 51 so as to enclose the reduced diameter section 51*a* of the tubular member body section 51. Therefore, the small diameter section 51*a* of the tubular member body section 51 constitutes an annular projected section projecting into the inside of the tubular member 5 and toward the proximal side. The annular projected section and the inner surface of the stent containing tubular member 5 (specifically, a distal portion of the tubular section 52) define an annular gap section therebetween. In addition, in this embodiment, the distal portions 69 (69*a*, 69*b*) of the pulling wires 6 (6*a*, 6*b*) are fixed at the outer surface of the small diameter section 51*a*. The gap section is filled with the fixing agent (adhesive), whereby the tubular member body section 51 and the tubular section 52 are united. In addition, the distal portions (fixation points) 69 (69*a*, 69*b*) of the pulling wires 6 (6*a*, 6*b*) described later are fixed to the tubular member 5 by the fixing agent or the like filling the annular gap section. As the fixing agent, there is preferably used an adhesive such as an epoxy resin, a UV-curing resin, a cyanoacrylate resin, etc., but the fixation may be made by fusing.

In the stent containing tubular member 5 used in this embodiment, the tubular member body section 51 and the tubular section 52 are approximately equal in outside diameter. The outside diameter of a stent containing part is preferably about 1.0 to 4.0 mm, particularly preferably 1.5 to 3.0 mm. In addition, the length of the stent containing tubular member 5 is preferably about 20 to 400 mm, particularly preferably 30 to 300 mm. The length of the tubular member body section 51 is preferably about 10 to 200 mm, particularly preferably 15 to 150 mm, and the length of the tubular section 52 is preferably about 10 to 200 mm, particularly preferably 15 to 150 mm.

The stent containing tubular member 5 is not limited to the one having the tubular member body section 51 and the tubular section 52 as above-mentioned, and it may be an integral one.

The slide tube 7 is so disposed that its distal end is proximate to the proximal end of the stent containing tubular member 5. In addition, the slide tube 7 can be contained in the fixing tube 8, from the proximal side thereof. The slide tube 7 may be one which can be fitted over the fixing tube 8, from the proximal side thereof. The slide tube 7 is capable of being moved toward the proximal side together with the stent containing tubular member 5 by pulling of the pulling wires 6, and is not fixed to the stent containing tubular member 5.

In addition, the stent delivery system 1 as shown in FIGS. 2 to 9 is configured so that the slide tube 7 includes the slide tube body 71, and a distal-side tubular member 72. The distal-side tubular member 72 is fixed to a distal portion of the slide tube body 71, covers the distal end of the slide tube body 71 and extends toward the distal side of the stent delivery system 1 relative to the distal end of the slide tube body 71. The distal-side tubular member 72 is an integrally molded tubular body having a reduced diameter section 73 which is located between the distal end and the proximal end of the distal-side tubular member 72 and which is reduced at least in inside diameter. In addition, in this embodiment, the inside diameter of the reduced diameter section 73 is approximately equal to, or slightly greater than or slightly smaller than the inside diameter of the slide tube body 71. Further, in the stent delivery system 1 according to this embodiment, as shown in FIGS. 2 to 9, the distal-side tubular member 72 is, at least at its sections other than the reduced diameter section 73, greater than the slide tube body 71 in outside diameter and in inside diameter. The reduced diameter section 73 is located between the distal end and the proximal end of the distal-side tubular member 72, specifically, located at a position slightly on the proximal side relative to the distal end of the distal-side tubular member 72.

In addition, in the stent delivery system 1 according to this embodiment, the ring-shaped member 41 is contained between the distal end of the slide tube body 71 and the reduced diameter section 73 of the distal-side tubular member 72. The pulling wires 6*a* and 6*b* are fixed to the ring-shaped member 41. In addition, the inside diameter of the reduced diameter section 73 of the distal-side tubular member 72 is greater than the outside diameter of the distal-side tube 2. Therefore, the distal-side tubular member 72 can be moved toward the proximal side without contacting the distal-side tube 2. The inside diameter of the reduced diameter section 73 of the distal-side tubular member 72 is smaller than the outside diameter of the ring-shaped member 41. Therefore, the reduced diameter section 73 restricts movement of the ring-shaped member 41 toward the distal side. In addition, with the pulling wires 6*a* and 6*b* pulled toward the proximal side, the slide tube 7 is moved toward the proximal side together with the ring-shaped member 41. The ring-shaped member 41 is not fixed to either the slide tube body 71 or the distal-side tubular member 72, but is rotatably contained between the distal end of the slide tube body 71 and the reduced diameter section 73 of the distal-side tubular member 72. The ring-shaped member 41 is this rotatable about its axis. The distal-side tubular member 72 of the slide tube 7 permits turning of the ring-shaped member 41, and large movement of the ring-shaped member 41 along the axial direction is substantially inhibited by the reduced diameter section 73 and the distal end of the slide tube body 71. Thus, the ring-shaped member 41 is turnable relative to the slide tube 7, to thereby help ensure that even when the distal-side tubular member 72 (slide tube 7) is turned, the ring-shaped member 41 and the pulling wire fixation section and the pulling wires themselves are less liable to follow up to the turning.

The ring-shaped member 41 in this embodiment is composed of a plastic-made outer tube member 42, a plastic-made inner tube member 43 inserted in the plastic-made outer tube member 42, and an adhesive 44 filling the gap between the plastic-made outer tube member 42 and the plastic-made inner tube member 43. In addition, the pulling wires 6a and 6b pass between the plastic-made outer tube member 42 and the plastic-made inner tube member 43, and are fixed to the ring-shaped member 41 by the adhesive 44. The plastic-made outer tube member 42 and the plastic-made inner tube member 43 are preferably formed from a material which shows relatively little frictional resistance. Examples of the material which can be suitably used here include fluoro-polymers such as ETFE, etc., PEEK (polyethyer ether ketone), and polyimides.

Figure 9:
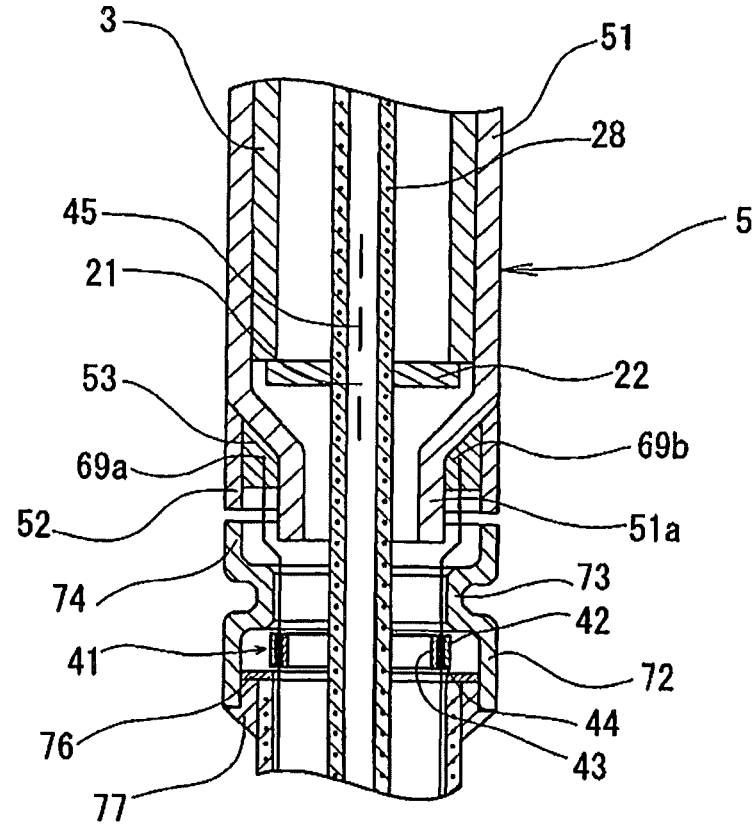
FIG. 9 is an enlarged cross-sectional view showing the vicinity of a proximal portion of a stent containing tubular member and a distal portion of a slide tube, of the stent delivery system of FIG. 1.

As shown in FIGS. 2 to 9, the slide tube 7 includes the slide tube body 71, and the distal-side tubular member 72 which is fixed to a distal portion of the slide tube body 71 and is greater than the slide tube body 71 in outside diameter and inside diameter. In this embodiment, as shown in FIG. 9, the distal-side member 72 of the slide tube 7 includes a distal portion 74, a proximal portion, and the reduced diameter section 73 between the distal portion and the proximal portion (specifically, at a position slightly on the proximal side relative to the distal end so that the reduced diameter section 73 is located closer toward the proximal portion). In this embodiment, the reduced diameter section 73 is reduced in both outside diameter and inside diameter. The reduced diameter section 73 may be reduced in only the inside diameter. As above-mentioned, the inside diameter of the reduced diameter section 73 is set to be greater in a certain extent than the outside diameter of the distal-side tube 2 and smaller than the outside diameter of the ring-shaped member 41. In addition, the reduced diameter section 73 extends along the axial direction while retaining a substantially uniform inside diameter over a predetermined length. Therefore, deformation of the distal-side tubular member 72 at the time of pulling of the pulling wires (in other words, at the time of movement of the distal-side tubular member 72 toward the proximal side) is suppressed, and favorable movement is enabled. A proximal portion of the distal-side tubular member 72 is fixed to a distal portion of the slide tube body 71 by an adhesive 77. In addition, a resin ring 76 may be disposed between the ring-shaped member 41 and the distal end of the slide tube body 71, thereby preventing the adhesive 77 from flowing into the ring-shaped member 41.

Figure 5:
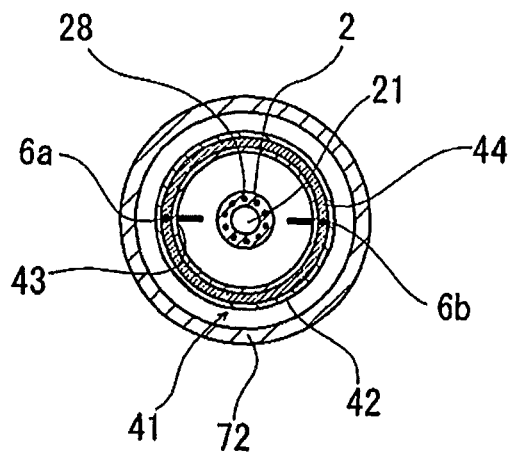
FIG. 5 is an enlarged cross-sectional view taken along the section line V-V in FIG. 2.
Figure 6:
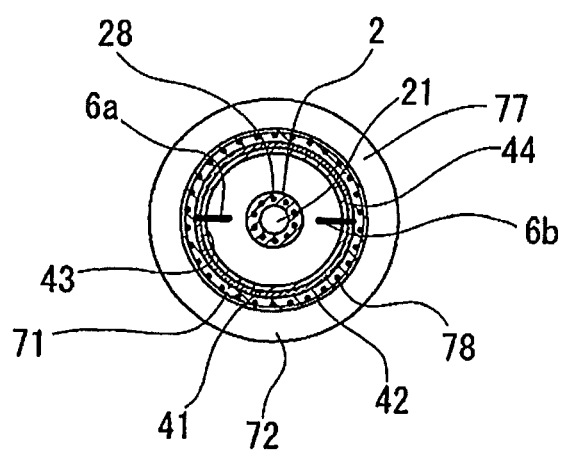
FIG. 6 is an enlarged cross-sectional view taken along the section line VI-VI in FIG. 2.

A distal portion of the slide tube body 71 enters into a proximal portion of the distal-side tubular member 72, and is spaced from the reduced diameter section 73 by a predetermined distance. This helps ensure that an annular cavity constituting a ring-shaped member holding section is formed between the distal portion of the slide tube body 71 and the reduced diameter section 73 of the distal-side tubular member 72. In addition, the ring-shaped member 41 is contained in the annular cavity constituting the ring-shaped member holding section. The ring-shaped member 41 is not fixed to either the slide tube body 71 or the distal-side tubular member 72 and is, therefore, turnable. However, movement of the ring-shaped member 41 along the axial direction inside the slide tube 7 is impossible, except for tiny movement corresponding to a clearance. As shown in FIG. 5, the pulling wires 6a and 6b are fixed to the inside of the ring-shaped member 41. With the pulling wires 6a and 6b pulled, the ring-shaped member 41 is also pulled, and the slide tube 7 is, by being pushed from the distal side by the ring-shaped member 41, also moved toward the proximal side of the stent delivery system 1.

In addition, the distal-side tubular member 72 of the slide tube 7 preferably has its distal portion 74 enclosing a proximal portion of the small diameter section 51a of the stent containing tubular member 5. The distal-side tubular member 72 of the slide tube 7 and the stent containing tubular member 5 are preferably not bonded to each other. In this embodiment, as shown in FIGS. 3, 4 and 9, the distal portion of the distal-side tubular member 72 of the slide tube 7 encloses the proximal portion of the small diameter section 51a of the stent containing tubular member 5 without being bonded to the latter and, further, substantially without making contact with the latter.

Furthermore, in this embodiment, a reinforcement layer 78 is provided over the whole of the slide tube body 71. With such a reinforcement layer thus provided, anti-kinking property is enhanced, and favorable sliding of the slide tube 7 is facilitated. The reinforcement layer is preferably a network-like reinforcement layer. The network-like reinforcement layer is preferably formed of braid wires. The braid wire is, for example, a wire braid, which can be formed from wire of a metal such as stainless steel, an elastic metal, a superelastic alloy, or a shape memory alloy having a wire diameter of 0.01 to 0.3 mm, preferably 0.03 to 0.2 mm. Or, alternatively, the braid wire may be formed from synthetic fiber such as polyamide fibers, polyester fibers, polypropylene fibers, etc.

In the stent delivery system 1 according to this embodiment, as shown in FIGS. 2 to 4, 7 and 10, the fixing tube 8 has a distal-side fixing tube 81 having a relatively large outside diameter, and a proximal-side fixing tube 82 fixed to a proximal portion of the distal-side fixing tube 81. In addition, the distal-side fixing tube 81 has a distal reduced diameter section 81a, and an inner surface of the distal reduced diameter section 81a is in contact with the outer surface of a proximal portion of the slide tube 7. The slide tube 7 is not fixed to the distal-side fixing tube 81, and, by sliding toward the proximal side, the slide tube 7 enters into and is contained in the distal-side fixing tube 81.

As in this embodiment, the slide tube 7 is preferably of the type of contained in the fixing tube 8 through sliding, but this is not restrictive. Another type may be adopted in which, with the slide tube slid toward the proximal side, the slide tube is fitted over the fixing tube.

Figure 10:
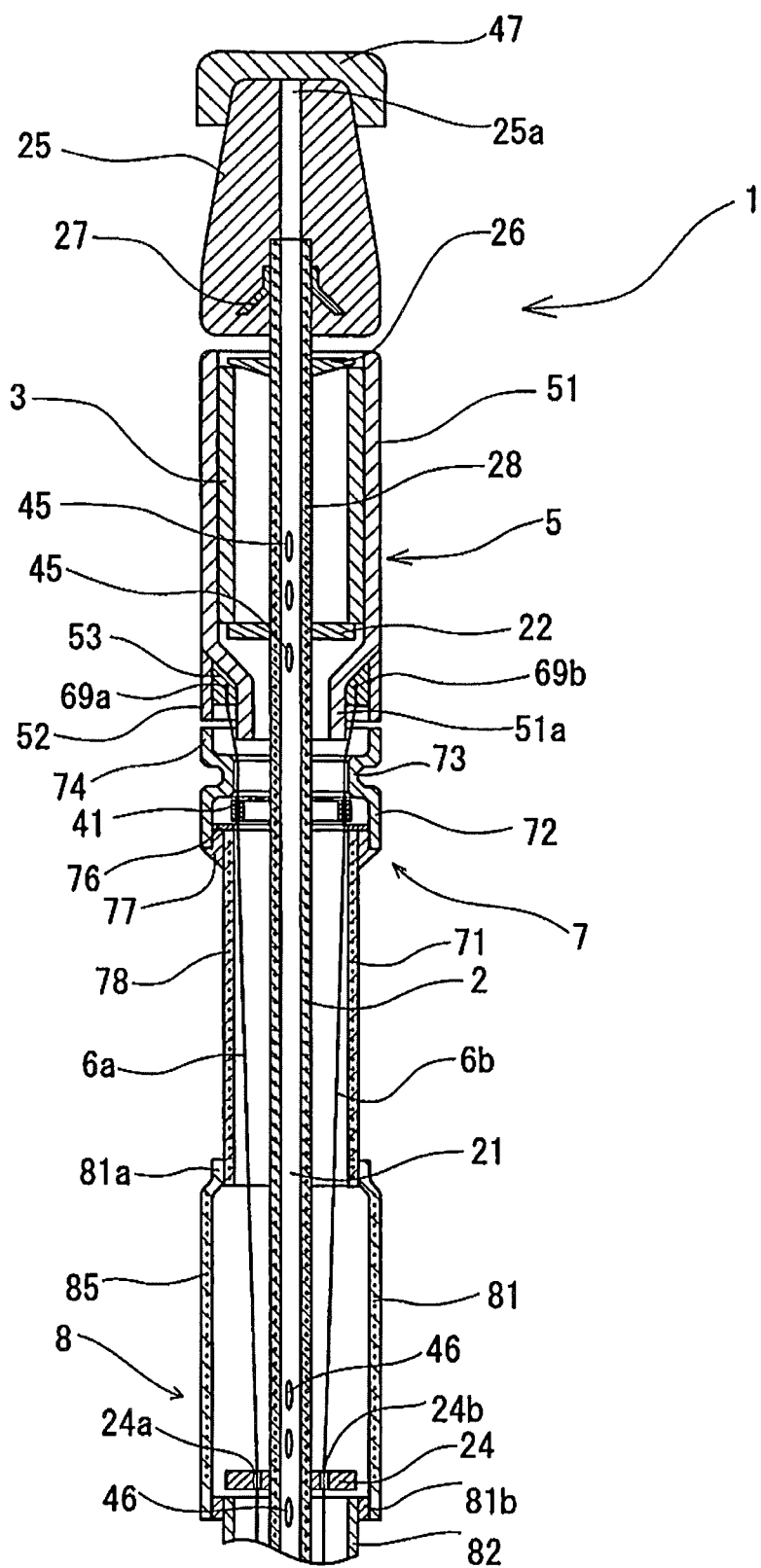
FIG. 10 is an enlarged cross-sectional view of a part of the stent delivery system illustrating operation of the stent delivery system according to one embodiment disclosed by way of example.

A distal portion of the proximal-side fixing tube 82 enters into the proximal end of the distal-side fixing tube 81, and is fixed to the proximal end of the distal-side fixing tube 81 by a fixing section 81b. In addition, the distal-side tube 2 is provided on its outer surface with a slide tube lock section 24 at a position in the fixing tube 8, specifically, at a position corresponding to a proximal portion of the distal-side fixing tube 81, as shown in FIG. 10. The slide tube 7 can be slid toward the proximal side (in the proximal direction) until it abuts on the slide tube lock section 24. In other words, by abutment on the slide tube lock section 24, the slide tube 7 is restricted from moving further toward the proximal side.

Further, in this embodiment, as shown in FIG. 10, a distal-side portion of the fixing tube 8, specifically, the distal-side fixing tube 81 is provided with a reinforcement layer 85 over substantially the whole thereof. The reinforcement layer is preferably a network-like one, a spiral one or the like. Particularly preferred is a network-like reinforcement layer. The network-like reinforcement layer is preferably formed in the shape of netting from fine metallic wire.

The fine metallic wire is preferably formed of stainless steel. Furthermore, as shown in FIG. 10, it is preferable that the reinforcement layer is absent at the part which becomes a joint part for connection with the proximal-side fixing tube 82.

Figure 7:
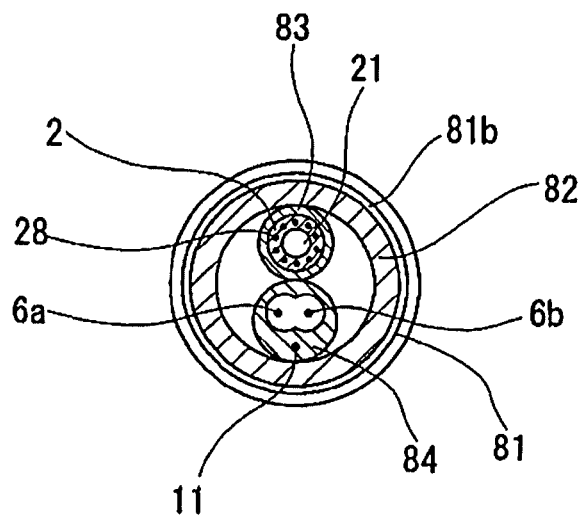
FIG. 7 is an enlarged cross-sectional view taken along the section line VII-VII in FIG. 2.
Figure 8:
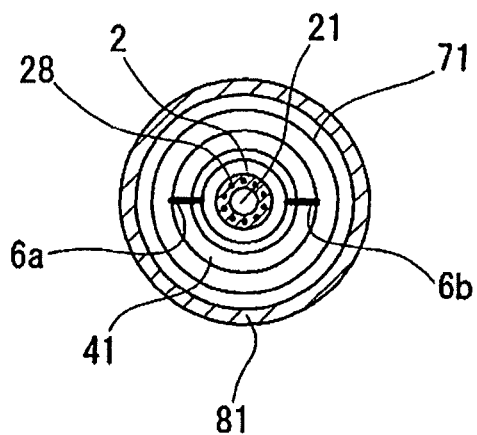
FIG. 8 is an enlarged cross-sectional view taken along the section line VIII-VIII in FIG. 2.

A proximal portion of the distal-side tube 2 is provided with a tubular firm attachment member 83 which contains the proximal portion of the distal-side tube 2. The distal end of the proximal end tube 4 is provided with a tubular fixing member 84. In addition, as shown in FIGS. 4 and 7, the tubular firm attachment member 83 and the tubular fixing member 84 are firmly attached to the proximal-side fixing tube 82.

As shown in FIGS. 2 and 3, in this stent delivery system 1, a plurality (specifically, two) of the pulling wires 6a and 6b are provided. The pulling wires 6a and 6b have their parts at the fixation points 69a and 69b fixed to the outside of a small diameter portion of the stent containing tubular member 5 by the fixing agent 53, in a gap section of the tubular member 5 as above-mentioned. In addition, the pulling wires 6a and 6b are spaced from each other by a predetermined length, and the fixation points 69a and 69b are spaced from each other by a predetermined length.

Materials for forming the stent containing tubular member 5 (tubular member body section 51, tubular section 52), the slide tube 7 (slide tube body 71, distal-side tubular member 72) and the fixing tube 8 (distal-side fixing tube 81, proximal-side fixing tube 82) are selected taking into account the physical properties (flexibility, hardness, strength, sliding properties, anti-kinking property, stretching properties) required of the stent containing tubular member. Examples of materials include polyethylene, polypropylene, nylon, polyethylene terephthalate, polyimides, fluoro-polymers such as PTFE, ETFE, etc., and thermoplastic elastomers are used preferably. The thermoplastic elastomers are appropriately selected from among nylon-based ones (e.g., polyamide elastomers), urethane-based ones (e.g., polyurethane elastomer), polyester-based ones (e.g., polyethylene terephthalate elastomer), and olefin-based ones (e.g., polyethylene elastomer, polypropylene elastomer).

Further, an outer surface of the stent containing tubular member 5 is preferably subjected to a treatment for making the surface show lubricating properties. Examples of such a treatment include a method in which a hydrophilic polymer such as polyhydroxyethyl methacrylate, polyhydroxyethyl acrylate, hydroxypropyl cellulose, methyl vinyl ether-maleic anhydride copolymer, polyethylene glycol, polyacrylamide, polyvinylpyrrolidone, etc. is coated to or fixed to the outer surface. In addition, the above-mentioned hydrophilic polymer may be coated to or fixed to an inner surface of the stent containing tubular member 5, for promising better sliding of the stent 3.

The stent containing tubular member 5 may be formed by use of a combined two-layer structure of the above-mentioned polymers (e.g., an outer surface formed of nylon and an inner surface formed of PTFE).

In addition, the stent delivery system 1 has the pulling wires 6 each of which has one end section fixed to a proximal portion of the stent containing tubular member 5, extends beyond the proximal end of the stent containing tubular member 5, penetrates the slide tube 7 and the fixing tube 8, and extends inside the proximal-side tube 4. With the pulling wires 6 pulled toward the proximal side of the proximal-side tube, the stent containing tubular member 5 and the slide tube 7 are moved toward the proximal side.

In addition, as shown in FIGS. 1 to 3 and 5 to 10, in this stent delivery system 1, a plurality (specifically, two) of pulling wires 6a and 6b are provided, and the pulling wires 6a and 6b are fixed to a proximal portion of the stent containing tubular member 5 by the fixation points 69a and 69b provided at portions near the stent. As mentioned, the pulling wires 6a and 6b are, and the fixation points 69a and 69b are, so disposed as to be spaced from each other by a predetermined distance.

Further, in this embodiment, the pulling wires 6a and 6b are fixed also to a member or members to be moved by pulling. Specifically, as shown in FIG. 9 and above-mentioned, the pulling wires 6a and 6b are fixed also to the ring-shaped member 41 possessed by the slide tube 7. In the stent delivery system 1 according to this embodiment, therefore, with the pulling wires 6a and 6b pulled toward the proximal side, the ring-shaped member 41 is also pulled toward the proximal side, and, due to the abutment of the slide tube 7 (slide tube body 71) on the ring-shaped member 41, the slide tube is also pulled toward the proximal side (in the proximal direction). In this embodiment, accordingly, the stent containing tubular member 5 and the slide tube 7 are pulled separately from each other, and the stent containing tubular member 5 and the slide tube 7 do not make contact with each other at the time of pulling. In addition, the forces at the time of pulling of the pulling wires 6a and 6b are dispersed to the fixation points 69a and 69b and to the fixation section of the ring-shaped member 41 which is a member moved by pulling, so that the fixation between the pulling wires 6a, 6b and the stent containing tubular member 5 at the fixation points 69a, 69b is securely prevented from being released.

In the stent delivery system 1 according to this embodiment, as shown in FIG. 1, the pulling wires 6 penetrate the proximal-side tube 4, and extend beyond the proximal end of the proximal-side tube.

The material constituting the pulling wire can be a wire or a strand of a plurality of wires. The outer diameter of the pulling wire is not particularly limited. Normally, it is preferably about 0.01 to 0.55 mm, more preferably about 0.1 to 0.3 mm.

Examples of the material forming the pulling wires 6 include stainless steel wires (preferably, high tensile stainless steel for springs), piano wires (preferably, nickel-plated or chromium-plated piano wire), and superelastic alloy wires; wires of various metals such as Ni—Ti alloy, Cu—Zn alloy, Ni—Al alloy, tungsten, tungsten alloys, titanium, titanium alloys, cobalt alloys, tantalum, etc.; polymer materials having comparatively high rigidity such as polyamides, polyimides, ultra-high-molecular-weight polyethylene, polypropylene, fluoro-resins, etc.; and appropriate combinations thereof.

In addition, side surfaces of the pulling wires may be coated with a low-friction resin for increasing lubricity. Examples of the low-friction resin include fluoro-resins, 6,6-nylon, polyether ether ketone, and high-density polyethylene. Among these, preferred are fluoro-resins. Examples of the fluoro-resins include polytetrafluoroethylene, polyvinylidene fluoride, ethylene-tetrafluoroethylene, and perfluoroalkoxyresins. Besides, coatings of silicone and various hydrophilic resins may also be adopted.

The stent delivery system 1 according to this embodiment includes a rigidity-imparting body 11 separate from the above-mentioned pulling wires. As shown in FIGS. 1, 4 and 7, the rigidity-imparting body 11 extends from the proximal side of the stent delivery system 1, passes through the inside of the proximal-side tube 4 and, further, enters into the fixing tube 8. In addition, as shown in FIG. 4, the distal end 11a of the rigidity-imparting body 11 is fixed to the slide tube lock section 24. The distal end 11a of the rigidity-imparting body 11 is fixed preferably by embedding it in the material forming the slide tube lock section 24. As shown in FIG. 3, the pulling wires 6a and 6b are not fixed to the slide tube lock section 24, but pass through passages 24a and 24b formed in the slide tube lock section 24.

In the stent delivery system 1 according to this embodiment, as shown in FIG. 4, the rigidity-imparting body 11 is fixed also to the tubular fixing member 84 fixed to the fixing tube 8. As shown in FIG. 4, the tubular fixing member 84 is formed with or includes a rigidity-imparting body fixing section 84a which extends over a predetermined length along the axial direction. Thus, a distal portion of the rigidity-imparting body 11 is fixed at two positions, whereby a strong reinforcing effect is exhibited by the distal portion of the rigidity-imparting body 11. Particularly, it reinforces the slide tube lock section 24 when the slide tube 7 abuts on the slide tube lock section 24.

In addition, the rigidity-imparting body 11 is preferably fixed at its proximal portion to a proximal portion of the proximal-side tube 4 or to the operating section 10 which will be described later. With such a rigidity-imparting body 11 provided, deformation of the stent delivery system at the time of pulling of the pulling wires can be restrained. The distal end 11a of the rigidity-imparting body 11 may be formed to be a flat section, in order to make assured the fixation by the slide tube lock section 24. Further, the rigidity-imparting body 11 may be formed with a wavy part at a side surface thereof, as a means for preventing the rigidity-imparting body 11 from slipping off the fixing member.

The rigidity-imparting body 11 can be a wire or a strand of a plurality of wires. In addition, the thickness (diametral size) of the rigidity-imparting body 11 is not particularly limited; normally, it is preferably about 0.01 to 1.5 mm, more preferably about 0.1 to 1.0 mm.

The rigidity-imparting body 11 is preferably high in rigidity (for example, possessing a relatively larger wire diameter) at its body-side portion (specifically, a portion to be located inside the proximal-side tube) and low in rigidity (possessing a relatively smaller wire diameter) at its distal-side portion. Further, it is preferable that a tapered section where the wire diameter varies in a tapered manner is present at a transition point between the body-side portion and the distal-side portion.

In addition, examples of the material for forming the rigidity-imparting body 11 include stainless steel wires (preferably, high tensile stainless steel for springs), piano wires (preferably, nickel-plated or chromium-plated piano wire), superelastic alloy wires, and wires of various metals such as Ni—Ti alloy, Cu—Zn alloy, Ni—Al alloy, tungsten, tungsten alloys, titanium, titanium alloys, cobalt alloys, tantalum, etc. Besides, the rigidity-imparting body 11 is preferably harder than the pulling wires.

The stent 3 is contained in the stent containing tubular member 5.

Figure 15:
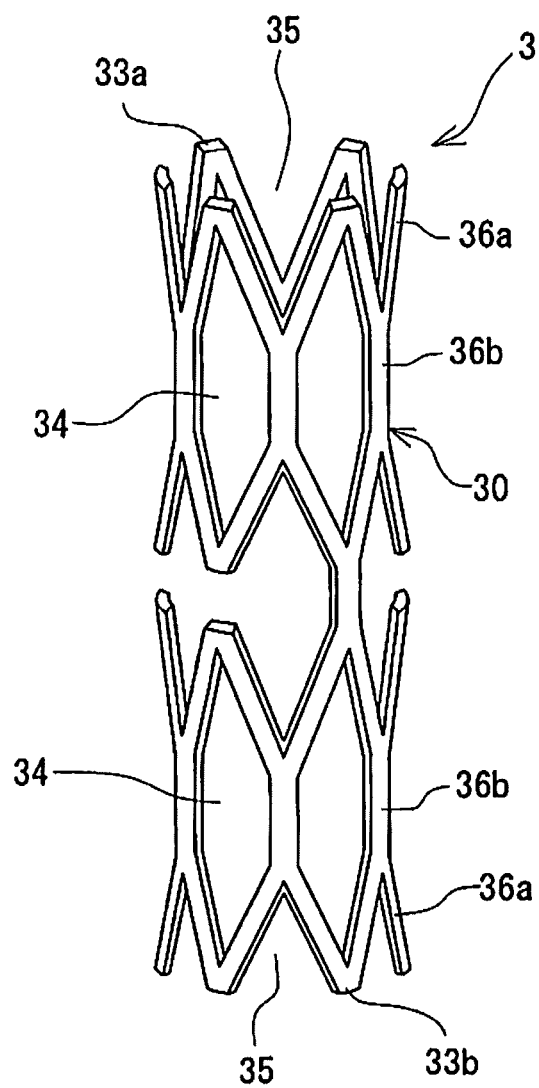
FIG. 15 is a side view of an example of a stent used in the stent delivery system disclosed here.

The stent 3 may be any stent that is a so-called self-expandable type stent. For instance, as the stent 3, one that is shaped as shown in FIG. 15 (showing a stent in a state of having been restored to its pre-compression shape by expansion) can be used suitably. The stent 3 in this example includes a cylindrical frame body 30, openings 34 demarcated (surrounded) by frames 36a and 36b constituting the cylindrical frame body 30, and cutouts 35 surrounded by the frames 36a. The frame body 30 has both end sections 33a and 33b.

The stent is produced, for example, by preparing a superelastic alloy-made metallic pipe (described later) having an outside diameter conforming to an in-vivo part where the stent is to be indwelled, and removing spaced apart potions of the side surface of the pipe by cutting (for example, mechanical cutting, laser beam cutting), chemical etching or the like to form a plurality of cutouts or a plurality of openings in the side surface.

Since the stent 3 has the cutouts 35 at the end sections of the frame body 30, deformation of the end sections 33a and 33b of the stent 3 is facilitated; particularly, the end sections become capable of partial deformation, so that the stent 3 shows good response to deformation of the blood vessel in which it is put indwelling. In addition, since the end sections 33a and 33b are formed of end sections of a plurality of the frames 36a, they are less liable to collapse, and have sufficient strength. The openings 34 surrounded by the frames 36a and 36b are formed between both the end sections, and the openings 34 are relatively easily deformed by deformation of the frames 36a. Therefore, the stent 3 is easily deformed also at its central section (central section of the frame body 30). The shapes and the numbers of the cutouts and the openings are not limited to those shown in the figure; the number of the cutouts is preferably about 3 to 10, and the number of the openings is preferably about 3 to 10.

The frame body 30 has an outside diameter of 2.0 to 30 mm, preferably 2.5 to 20 mm, an inside diameter of 1.4 to 29 mm, preferably 1.6 to 28 mm, and a length of 10 to 150 mm, preferably 15 to 100 mm.

The shape of the stent is not restricted to the one shown in FIG. 15. Examples of the applicable stent shape include one in which trapezoidal cutouts are formed at both end portions and a plurality of hexagonal openings are formed in a honeycomb-like pattern in a central portion, and one in which rectangular cutouts are formed in both end portions and a plurality of rectangular openings (two times the cutouts in length) are formed in a central portion. Further, the shape of the stent 3 is not restricted to the above-mentioned shapes, insofar as it can be reduced in diameter at the time of insertion and can be enlarged (restored) in diameter upon release into a living body. Examples of the applicable shape of the stent 3 include coil-like shapes, cylindrical shapes, roll-like shapes, irregular tubular shapes, supercoil-like shapes, leaf spring coil-like shapes, and basket- or mesh-like shapes.

As the material for forming the stent, superelastic alloys are used suitably. The term "superelastic alloy" used here means an alloy which is generally called shape memory alloy and which shows superelasticity at least at a living body temperature (around 37° C.). Particularly preferably, such superelastic alloys as Ti—Ni alloys containing 49 to 53 atomic % of Ni, Cu—Zn alloys containing 38.5 to 41.5 wt % of Zn, Cu—Zn—X alloys (X=Be, Si, Sn, Al, or Ga) containing 1 to 10 wt % of X, and Ni—Al alloys containing 36 to 38 atomic % of Al. Especially preferable are the above-mentioned Ti—Ni alloys. Besides, mechanical properties of the alloys can be appropriately changed by conversion of the Ti—Ni alloys into Ti—Ni—X alloys (X=Co, Fe, Mn, Cr, V, Al, Nb, W, B or the like) through replacing part of the Ti—Ni alloys with 0.01 to 10.0% of X, by conversion of the Ti—Ni alloys into Ti—Ni—X alloys (X=Cu, Pb, Zr) through replacing part of the Ti—Ni alloys with 0.01 to 30.0% of atoms, or by selection of a cold work ratio or/and final heat treatment conditions. In addition, mechanical properties of alloys can be appropriately changed by using the above-mentioned Ti—Ni—X alloys and selecting a cold work ratio and/or final heat treatment conditions.

The buckling strength (yield stress when load is applied) of the superelastic alloy to be used is 5 to 200 kgf/mm² (22° C.), more preferably 8 to 150 kgf/mm², and the restoring stress (yield stress when load is eliminated) of the superelastic alloy is 3 to 180 kgf/mm² (22° C.), more preferably 5 to 130 kgf/mm². The term "superelasticity" used here means a property of a material such that even after deformation (bending, stretching, or compression) of the material into a region in which ordinary metal is plastically deformed at a use temperature, release of the deformation results in that the material is restored substantially into its pre-compression shape without need for heating.

In addition, the stent to be used in the stent delivery system according here may include a stent body which is formed in a substantially cylindrical shape and which can be reduced in diameter, and a tubular cover (not shown) for sealing a side surface of the stent body.

Figure 12:
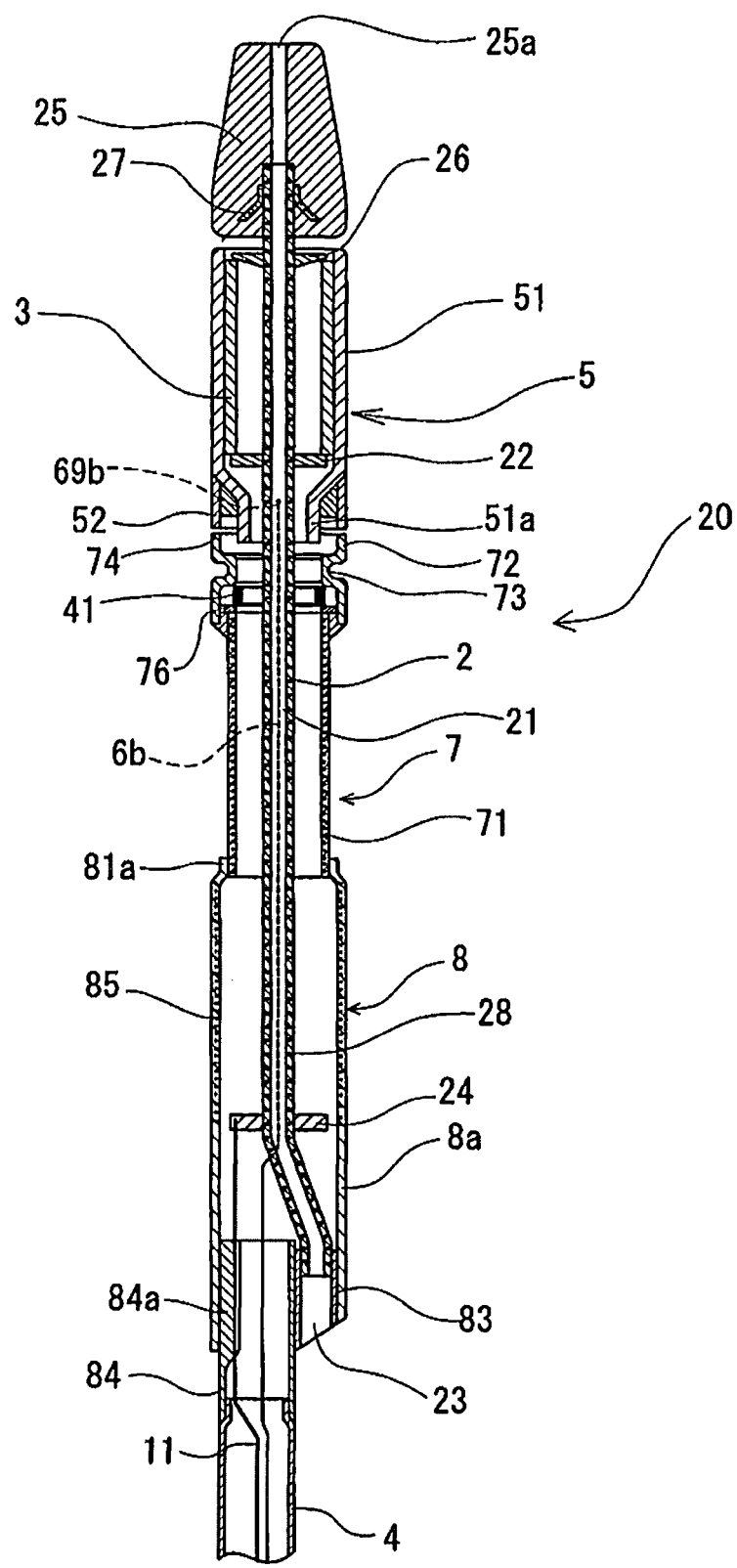
FIG. 12 is an enlarged cross-sectional view of a part of a stent delivery system according to another embodiment disclosed here by way of example.

The stent delivery system is not restricted to the above-described embodiment. For instance, it may be a stent delivery system 20 as shown in FIG. 12.

In the stent delivery system 20 according to this variation, the fixing tube 8 does not have a distal-side fixing tube 81 and a proximal-side fixing tube 82, but instead has an integrally formed fixing tube 8a, unlike in the above-described stent deliver system 1. In addition, as shown in FIG. 12, the fixing tube 8a is provided with a reinforcement layer 85 which extends from the distal end to the vicinity of a position where the slide tube lock section 24 is disposed. The reinforcement layer is the same as the above-described reinforcement layer.

Figure 13:
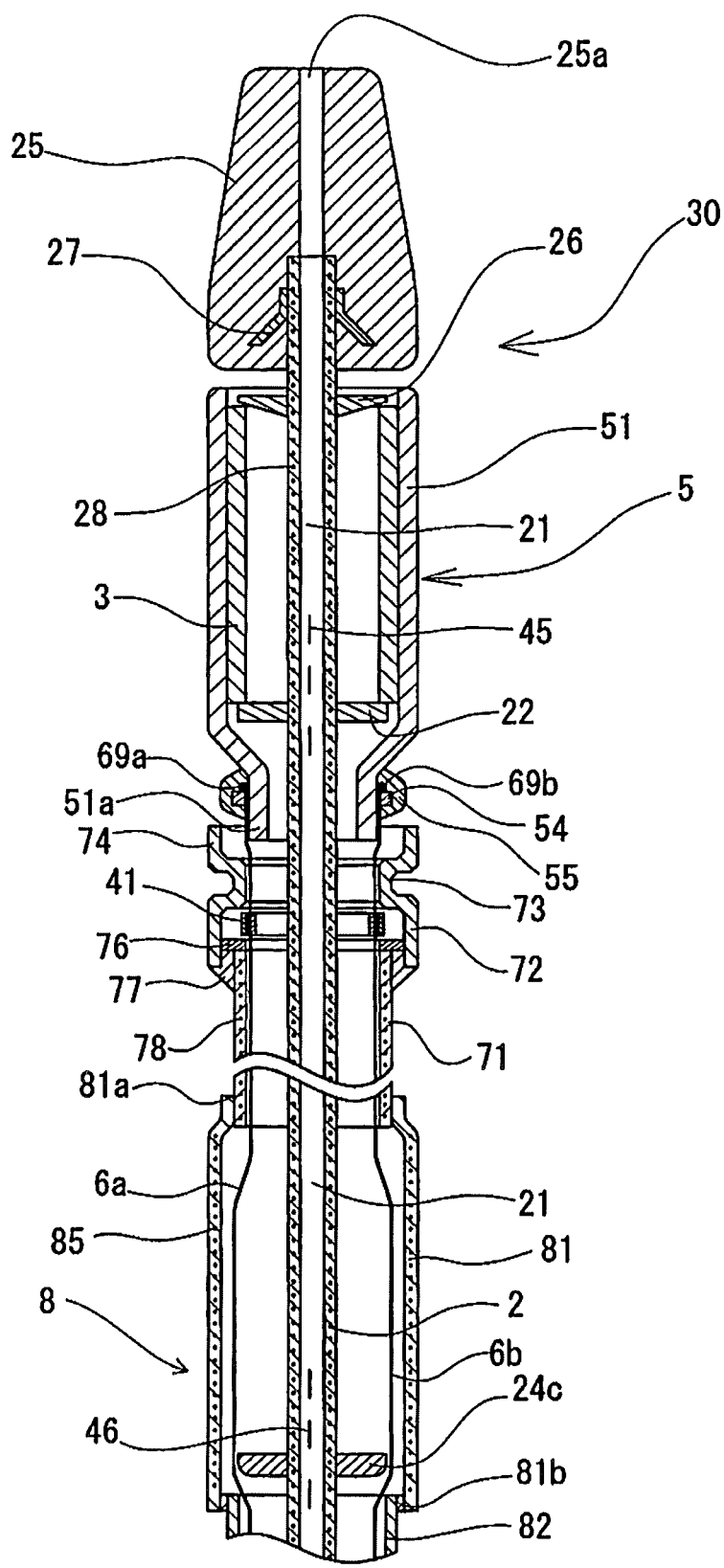
FIG. 13 is an enlarged cross-sectional view of a part of a stent delivery system according to a further embodiment disclosed here.

Furthermore, in all the above-described embodiments, the stent delivery system may be a stent delivery system 30 as shown in FIG. 13.

In the stent delivery system 30 according to this embodiment, the distal portions (69a, 69b) of the pulling wires 6a and 6b are fixed by a metallic ring 54 fixed to the small diameter section 51a of the stent containing tubular member 5. A coating section 55 formed of a resin or the like is provided on the outer surface of the metallic ring 54 so as to cover the metallic ring 54 and the distal ends of the pulling wires 6a and 6b, and prevent the metallic ring 54 and the distal ends of the pulling wires 6a and 6b from being exposed. In the stent delivery system 30 according to this embodiment, the tubular section 52 enclosing the small diameter section 51a of the stent containing tubular member 5 which has been possessed by the stent delivery system 1 is not provided.

In all the above-described embodiment, a slide tube lock section 24c of the stent delivery system 30 as shown in FIG. 13 may be adopted which does not have passages for permitting the pulling wires 6a, 6b to be passed therethrough; in this case, the pulling wires 6a, 6b pass on the outside of the slide tube lock section 24c.

Further, in all the above-described embodiment, a structure in which such a ring-shaped member 41 as abovementioned is not provided may also be adopted.

Figure 14:
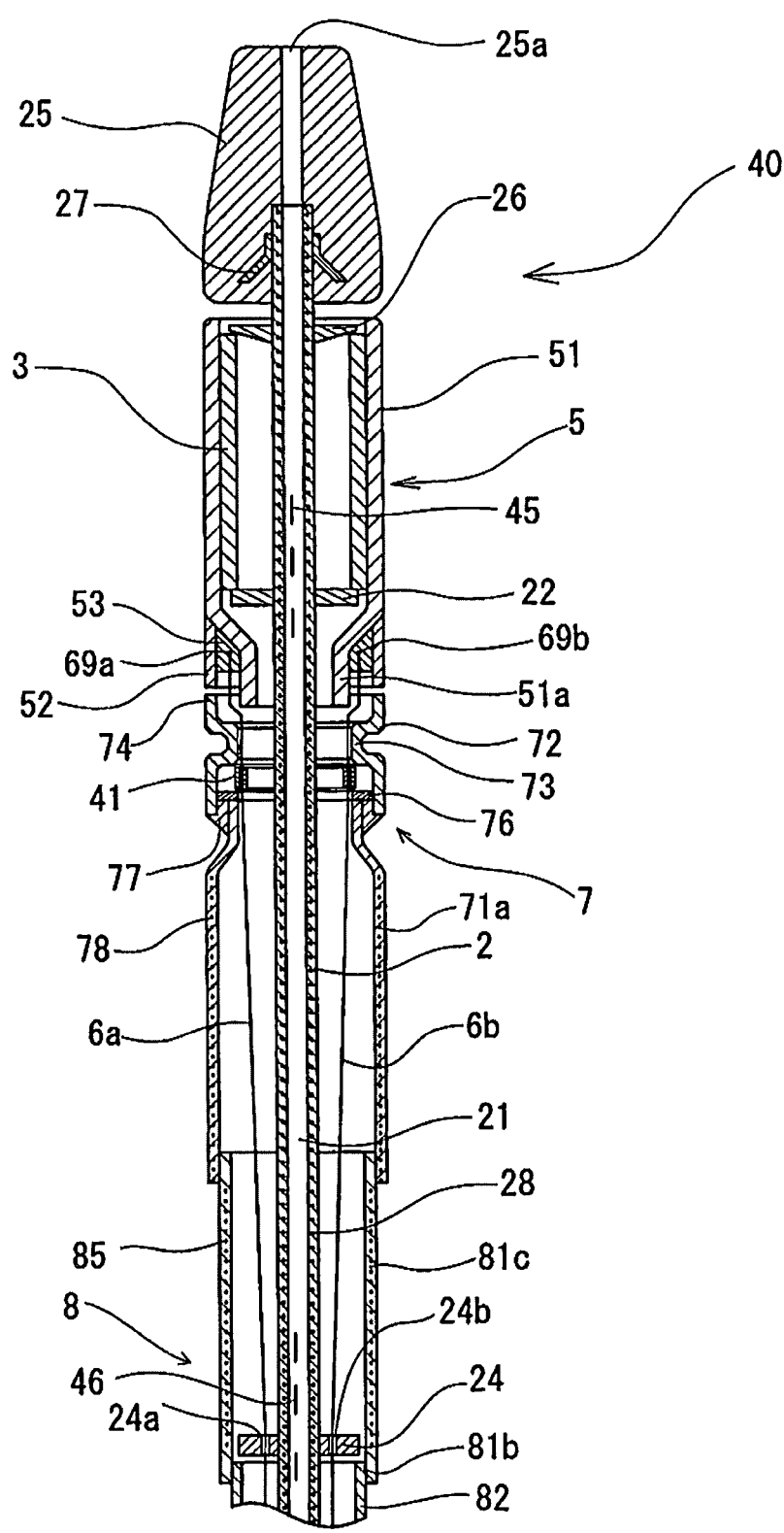
FIG. 14 is an enlarged cross-sectional view of a part of a stent delivery system according to a further another embodiment disclosed here.

Furthermore, in all the above-described embodiment, the stent delivery system may also be such a stent delivery system 40 as shown in FIG. 14.

In the stent delivery systems described above, the fixing tube 8 is of the type in which the slide tube 7 is contained in the fixing tube 8 starting from the proximal side of the slide tube at the time of pulling, specifically, the type in which the slide tube body 71 of the slide tube 7 enters the fixing tube 8 starting from the proximal end of the slide tube 7.

In contrast, in the stent delivery system 40 according to the embodiment shown in FIG. 14, the slide tube 7 is fitted over the fixing tube 8 starting from the proximal side of the slide tube at the time of pulling, specifically, the slide tube body 71a of the slide tube 7 encloses the distal-side fixing tube 81c of the fixing tube 8 starting from the proximal end of the slide tube.

Therefore, the inside diameter of the slide tube body 71a is approximately equal to or slightly greater than the outside diameter of the distal-side fixing tube 81c of the fixing tube 8. The distal-side fixing tube 81c is fixed at its proximal portion to a distal portion of the proximal-side fixing tube 82 by a fixing section 81b. In addition, in this embodiment, the member 24 does not function as a slide tube lock section.

All of the stent delivery systems 1 disclosed here include an operating section 10 fixed to the proximal end of a proximal-side tube 4. FIGS. 16-20 illustrate various aspects of the operating section 10.

The operating section 10 of the stent delivery system 1 in this embodiment includes, in addition to a pulling wire winding-up mechanism, a lock mechanism for unlockably locking the rotation of the pulling wire winding-up mechanism, and a reverse rotation restricting mechanism for restricting rotation in the reverse direction to a pulling wire winding-up direction of the pulling wire winding-up function.

Figure 16:
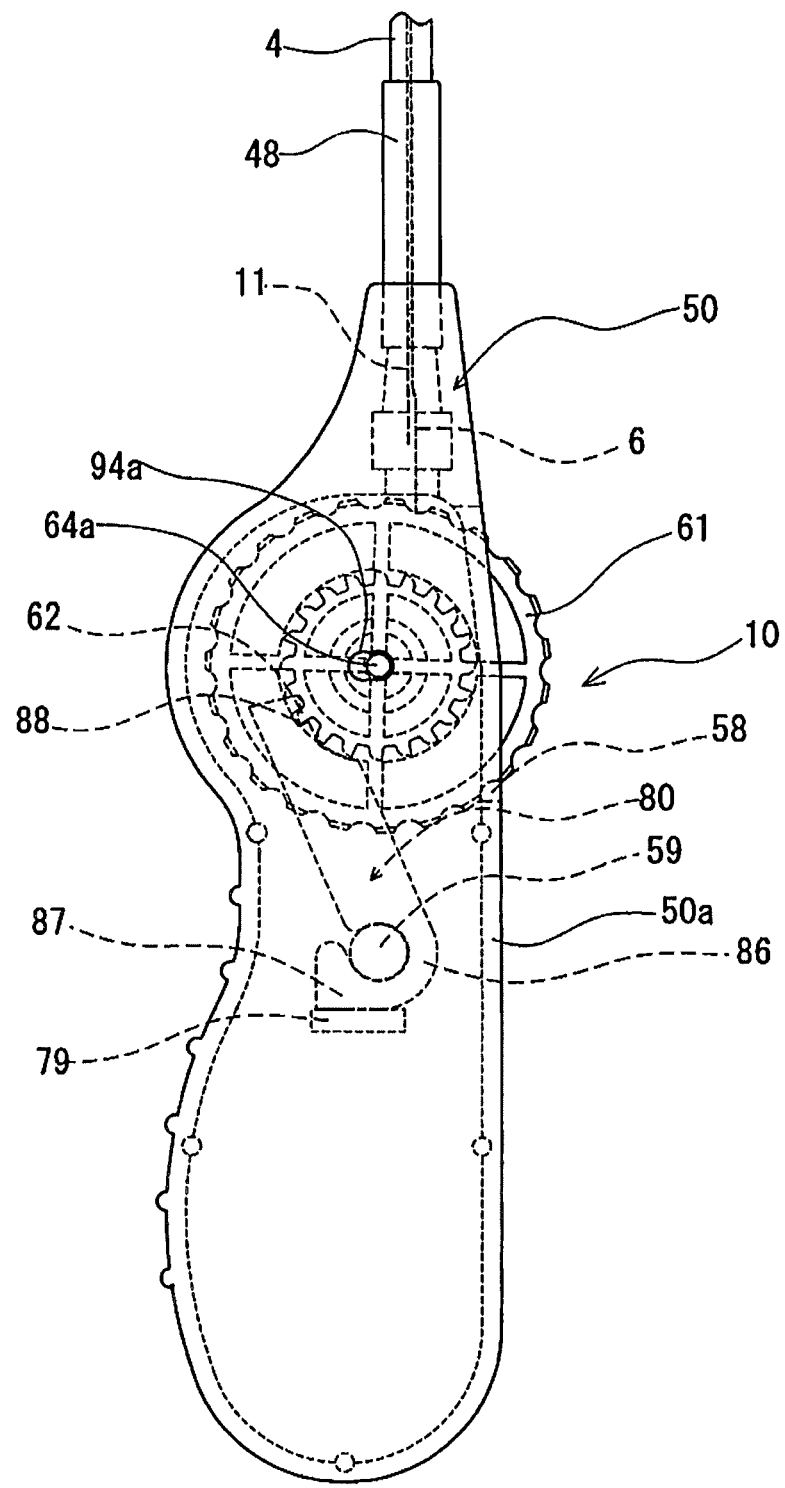
FIG. 16 is an enlarged front view in the vicinity of an operating section of the stent delivery system.

As shown in FIGS. 16-20, the operating section 10 has an operating section housing 50. The operating section housing 50 is composed of a first housing 50a and a second housing 50b. The operating section housing 50 has a shape which is rounded on the proximal end and has a recessed region (reduced outer dimension portion) at a central portion as shown in FIG. 16 so that the operating section housing 50 is gripped relatively easily and that a roller can be operated rather easily when the operating section housing 50 is being gripped.

Figure 18:
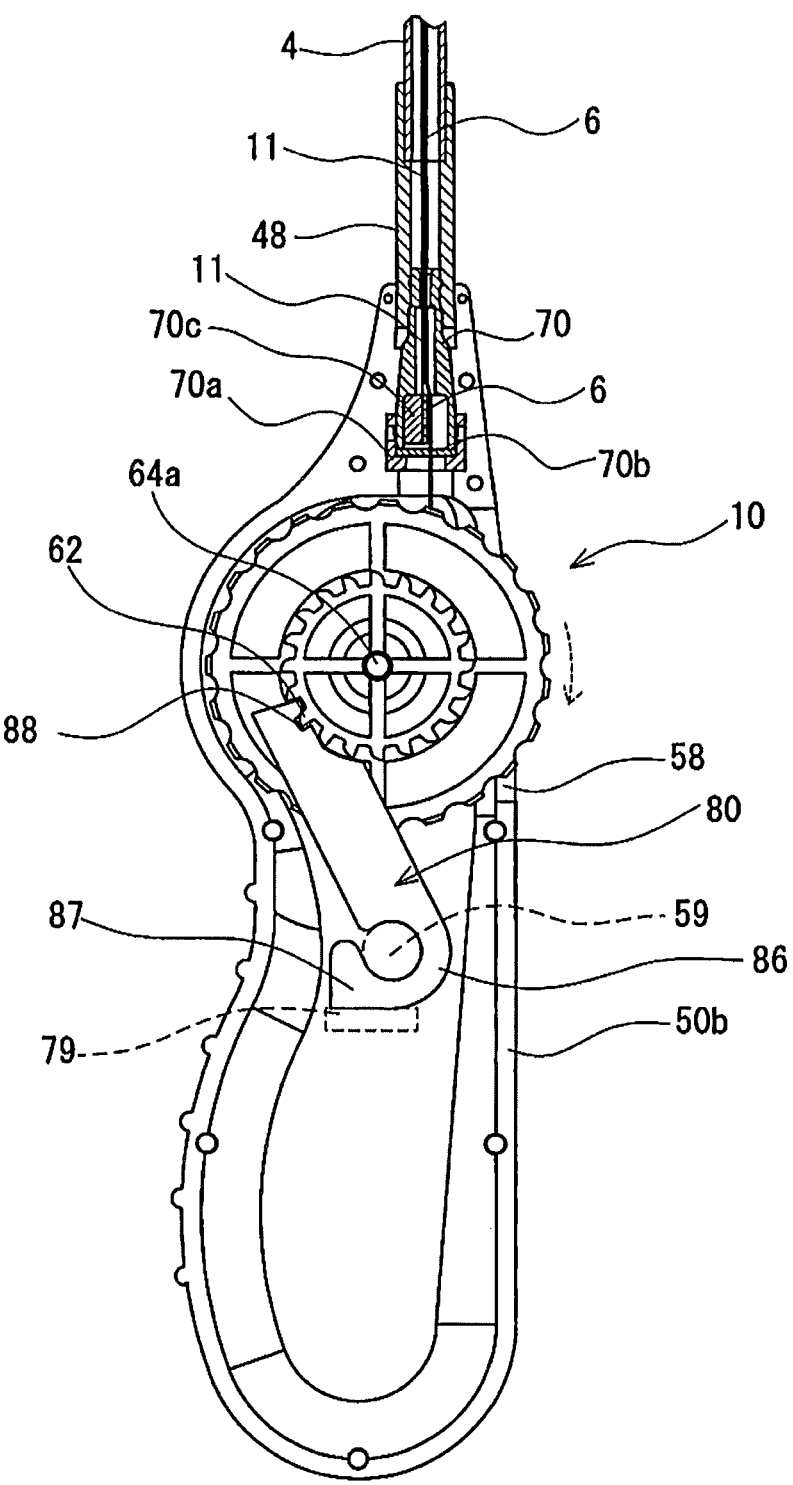
FIG. 18 is a partial cross-sectional view of the internal structure of the operating section of the stent delivery system shown in FIG. 16.

In addition, as shown in FIG. 18, a distal portion of a tubular connector 48 is fixed to the proximal end of the proximal-side tube 4. A seal mechanism connected to a proximal portion of the connector 48 is contained in the operating section housing 50. As shown in FIG. 18, the seal mechanism includes a seal mechanism tubular body member 70 having a distal portion fixed to a rear end section of the connector 48, a cap member 70a fixed to the proximal end of the tubular body member 70, a seal member 70h disposed between the tubular body member 70 and the cap member 70a, and a rigidity-imparting body fixing member 70c contained in the tubular body member. The body member 70 and the cap member 70a are each provided with an opening section penetrating throughout the length of each member. The seal member 70b is provided with hole sections or slits which permit the pulling wires 6 (6a, 6b) to pass therethrough in a liquid-tight condition and a slidable manner. In addition, a proximal portion of the rigidity-imparting body 11 is fixed to the rigidity-imparting body fixing member 70c. Besides, the rigidity-imparting body fixing member 70c is fixed in the tubular body member 70.

As shown in FIGS. 16-19, the housing 50 includes an opening section 58 through which an operating rotating roller 61 partly projects, a locking rib to engage projected portions of a gear section 62 provided on (fixed to) the roller 61, a bearing section 94b containing one end 64b of a rotating shaft of the roller 61, and a bearing section 94a containing the other end 64a of the rotating shaft of the roller

Figure 17:
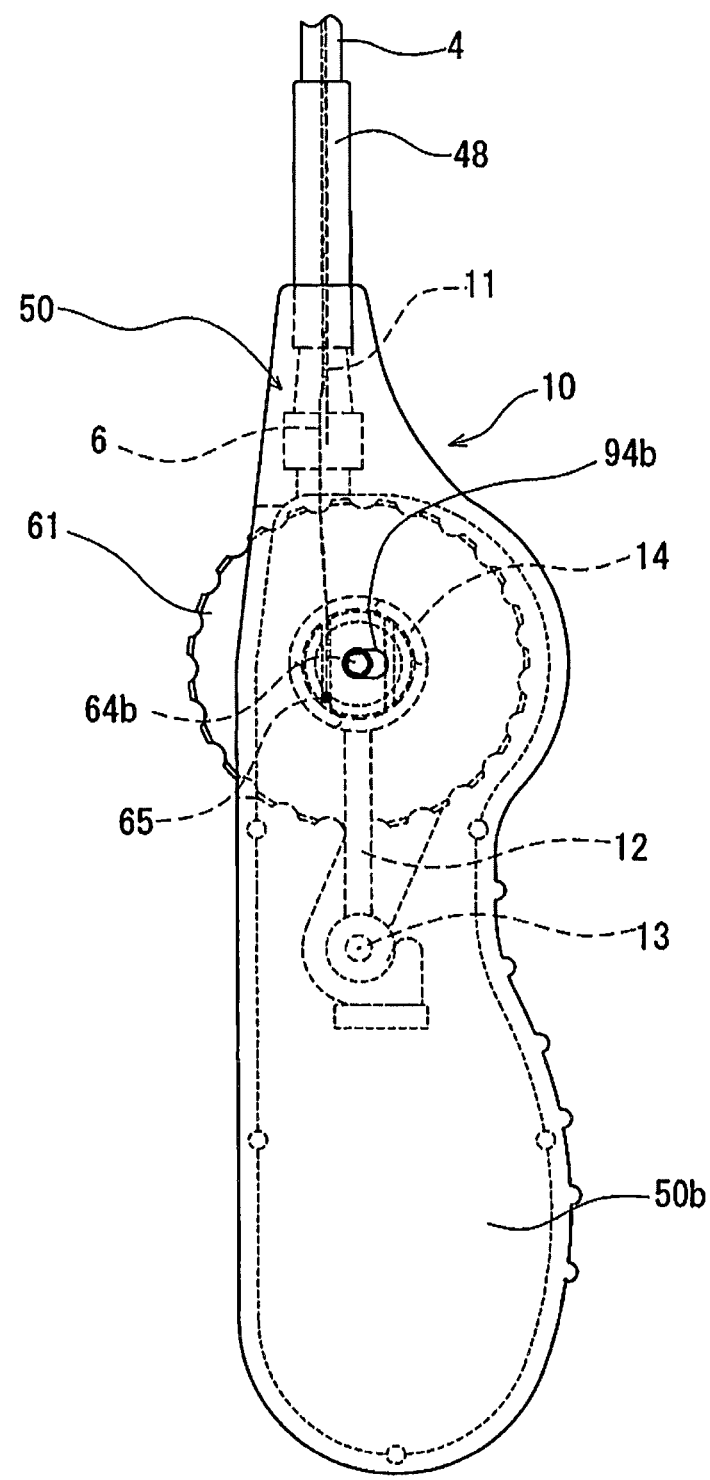
FIG. 17 is a rear view in the vicinity of the operating section of the stent delivery system shown in FIG. 16.

61. The locking rib is shaped to enter between the projected portions formed on the gear section 62 of the roller 61. In addition, as shown in FIGS. 16 and 17, the bearing sections 94*a* and 94*b* are gourd-shaped such that they contain the one end 64*b* and the other end 64*a* of the rotating shaft of the roller 61 and extend in the direction of spacing away from the above-mentioned opening section. The bearing sections 94*a* and 94*b* need not be gourd-shaped bearing sections and can be different shaped sections allowing movement over such a distance that engagement with the locking rib can be released. For example, the bearing sections 94*a* and 94*b* may be oblong, rectangular, elliptic or the like in shape. In the operating section 10 according to this embodiment, as shown in FIGS. 16 and 17, the above-described bearing sections 94*a* and 94*b* are gourd-shaped. Therefore, when the operating rotating roller 61 is pushed so that the ends 64*a* and 64*b* of the rotating shaft of the roller 61 which are contained in one-end-side spaces of the bearing sections 94*a* and 94*b* are caused to ride over facing rib portions formed at inside surfaces in central parts of the bearing sections 94*a* and 94*b*, the ends 64*a* and 64*b* of the rotating shaft of the roller 61 are contained in (positioned in) the other-end-side spaces of the bearing sections 94*a* and 94*b*. The condition shown in FIG. 18 is the condition where the roller 61 is pressed. In this condition, the roller 61 is pressed by a biasing member. However, since the ends 64*a*, 64*b* of the rotating shaft of the roller 61 make contact with the facing rib portions formed at the inside surfaces in the central parts of the bearing sections 94*a*, 94*b*, the ends 64*a*, 64*b* do not move into the one-end-side spaces of the bearing sections 94*a*, 94*b*. Accordingly, the roller 61 is kept in a rotatable state.

Figure 20:
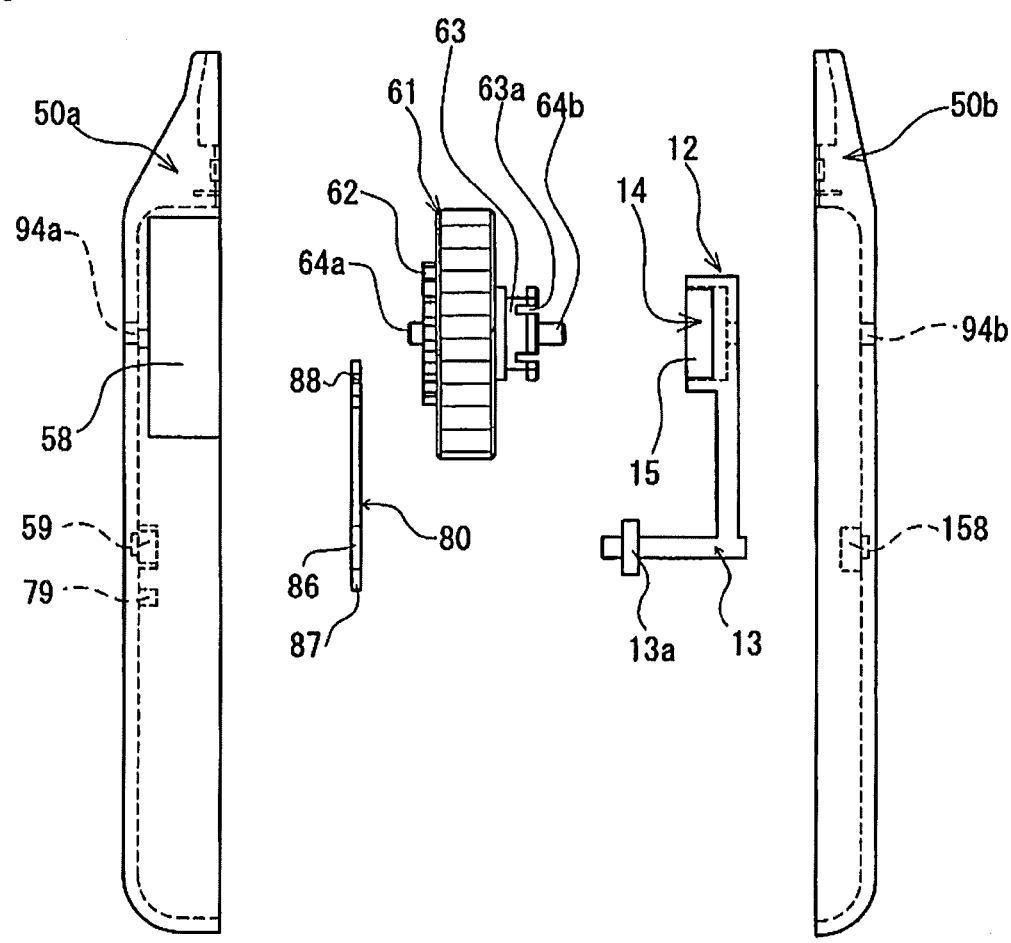
FIG. 20 is an exploded view of the internal structure of the operating section of the stent delivery system shown in FIG. 16.

In addition, in this embodiment, the operating section 10 has a collar member 12, as shown in FIGS. 17 and 20. The collar member 12 has a collar section 14 which contains a winding-up shaft section 63 and which defines an annular space between itself and the winding-up shaft section 63. The collar section 14 prevents the pulling wires wound up on the winding-up shaft section 63 from slackening. In addition, the collar member 12 has a function of guiding movement upon pressing of the rotating roller and a function of restraining the rotating roller from chattering. A pin 13 of the collar member 12 is borne by a projected part (bearing part) 59 of the first housing 50*a* and a recessed part (bearing part) 158 of the second housing 50*b*. As shown in FIGS. 16 and 17, the bearing sections 94*a*, 94*b* are formed in a gently circular shape, with the pin 13 (bearing parts 59, 158) as the center of the circle, and are formed to have a length permitting the roller 61 to be moved over a distance not smaller than the height of the locking rib. In addition, as shown in FIG. 20, the collar member 12 has two facing cutouts 15 ranging from side surfaces to a space inside the collar section 14. The pulling wires 6 each pass through one of the cutouts 15 and are fixed to the winding-up shaft section 63.

The pulling wire winding-up mechanism is composed of the roller 61 and the winding-up shaft section 63 rotated by rotation of the roller 61. The winding-up shaft section 63 grips or fixes proximal portions of the pulling wires 6. Specifically, as shown in FIG. 17, an anchor part 65 having a greater outer dimension or configuration than the pulling wire 6 is provided at a proximal portion of the pulling wire 6, and the winding-up shaft section 63 is provided with a slit(s) 63*a* in which the pulling wire 6 can be contained. In addition, the proximal portion of the pulling wire 6 is contained in the slit 63*a* in the winding-up shaft section 63 so that the anchor part 65 is located on the proximal outer side of the slit 63*a*. This helps ensure that when the winding-up shaft section 63 is rotated, the wire 6 is wound up onto the outer surface of the winding-up shaft section 63. The grip or fixation of the pulling wire 6 onto the winding-up shaft section 63 is not restricted to the above-mentioned arrangement, as other fixing arrangements can be employed. For example, the proximal end or a proximal portion of the pulling wire 6 may be directly fixed to the winding-up shaft.

The proximal portions of the pulling wires 6 to be wound up are preferably flexible, in order to facilitate the winding-up. The proximal portions of the pulling wires 6 can be made flexible by, for example, a method in which the proximal portions are formed from a flexible material, or a method in which the proximal portions are smaller in thickness (diameter size).

Figure 19:
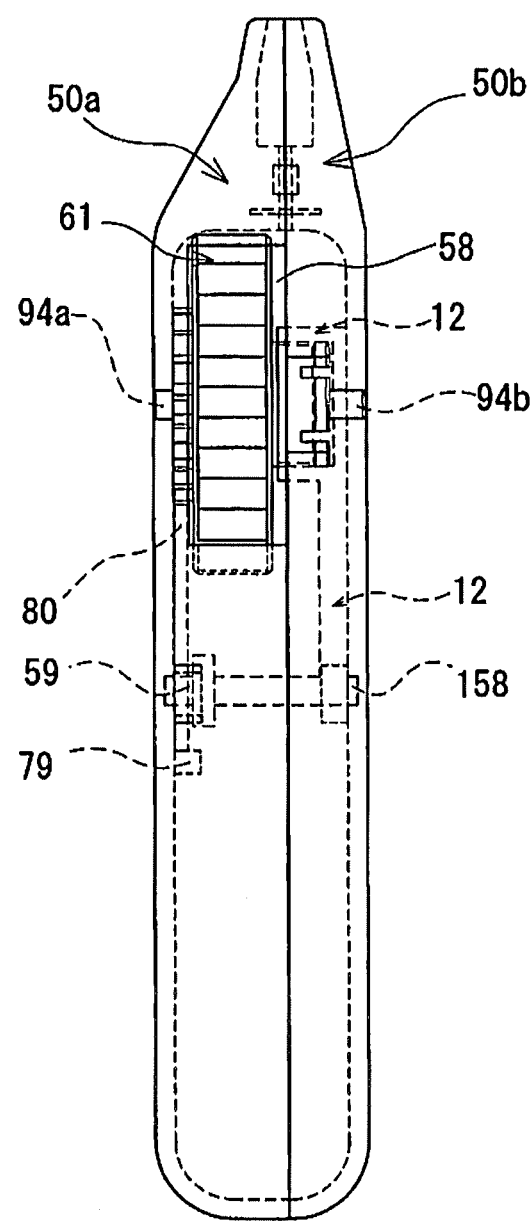
FIG. 19 is a right side view of only the operating section of the stent delivery system shown in FIG. 16.

In addition, in this embodiment, the winding-up shaft section 63 is formed integrally with the rotating roller 61, so that the winding-up shaft section 63 and the rotating roller 61 rotate together. The winding-up shaft section 63 is also coaxial with the rotating roller 61. Further, as shown in FIGS. 16, 18 and 19, the winding-up shaft section 63 is provided on one axial side surface of the rotating roller 61. With the rotating roller 61 rotated, the winding-up shaft section 63 is also rotated simultaneously. In addition, the amount of the pulling wire wound up on the winding-up shaft section 63 is preferably small, as compared with the rotational operating amount of the rotating roller. In other words, for a given amount of rotation of the rotating roller 61, the winding-up shaft section 63 rotates a smaller amount. This helps ensure that the pulling wires can be wound up slowly, and the movement of the stent containing tubular member toward the proximal side is relatively slow and favorable. In this embodiment, the outside diameter of the winding-up shaft section is smaller than the outer diameter of the rotating roller, so that the amount of the pulling wires wound up is relatively small as compared with the rotational operating amount of the rotating roller.

The outside diameter of the winding-up shaft section 63 is preferably about 1 to 60 mm, particularly preferably 3 to 30 mm, and the outside diameter of the rotating roller 61 is preferably about 1 to 20 times larger than, particularly preferably 1 to 10 times larger than, the outside diameter of the winding-up shaft section. In addition, the outside diameter of the rotating roller is preferably about 10 to 60 mm, particularly preferably 15 to 50 mm.

The rotating roller and the winding-up shaft section are not restricted to an integral construction, and the winding-up shaft section may be one composed of a separate member which is rotated following the rotation of the rotating roller. The transmission system for rotation of the rotating roller in such a configuration may be a gear type or belt type. The surface part which may be contacted at the time of operating the roller 61 is preferably a surface which is difficulty slidable. For instance, the surface part which may be contacted at the time of operating the roller 61 is preferably subjected to a knurling treatment, an embossing treatment, coating with a high-friction material, or the like so that user's fingers are not liable to slip while operating the roller 61.

In addition, the operating section 10 according to this embodiment includes a locking mechanism for unlockably locking the rotation of the pulling wire winding-up mechanism, and a reverse rotation restricting mechanism for restricting rotation in the reverse direction to the pulling wire winding-up direction of the pulling wire winding-up function.

As shown in FIGS. 16-18, the operational rotating roller 61 has the gear section 62 which turns coaxially and integrally with the operational rotating roller 61. Further, as shown in FIGS. 19 and 20, the gear section 62 is provided on the other axial side surface of the rotating roller 61 (in other words, at the surface on the side axially opposite to the surface at which the winding-up shaft section 63 is located). Therefore, the gear section 62 and the winding-up shaft section 63 are separated or partitioned from each other by a wall constituted by the operating roller section.

The operational rotating roller 61 is partly exposed via the opening section, and the exposed part constitutes an operating section. And the rotating roller has the other end 64a of the rotating shaft which is provided on one side surface (specifically, the side surface of the gear section 62) and one end 64b of the rotating shaft which is provided on the other side surface (specifically, the side surface of the winding-up shaft 63a).

The interior of the housing 50 is provided with biasing means (biasing member) 80 for biasing the rotating roller 61 toward the opening section of the housing. Specifically, the roller 61 is biased by the biasing means 80. Further, the housing 50 is provided with a locking rib which enters between the projected parts of the gear section 62 of the rotating roller 61 biased by the biasing member 80. Therefore, in the state of being biased by the biasing member 80, the rotating roller 61 is in the state shown in FIG. 17, wherein the locking rib engages the projected parts of the gear section 62, so that the rotating roller 61 is non-rotatable or is in a non-rotatable state. When the rotating roller 61 is pushed in the direction of spacing away from the locking rib, the one end 64b and the other end 64a of the rotating shaft of the rotating roller are moved inside the bearing sections 94a and 94b provided in the housing 50, resulting in the rotating roller 61a being shifted to a rotatable state. Therefore, the operating section 10 in this embodiment restricts rotation in the state of not pressing the rotating roller 61 (i.e., when the operator/user is not operating the roller 61) and has the locking mechanism which unlockably locks the rotation of the pulling wire winding-up mechanism.

Furthermore, in the operating section according to this embodiment, the above-mentioned biasing means 80 and the above-mentioned gear section 62 constitute the reverse rotation restricting mechanism for restricting rotation in the reverse direction to the pulling wire winding-up direction of the pulling wire winding-up function.

As shown in FIGS. 16-18, the operating section 10 is provided with the reverse rotation restricting mechanism. In the operating section 10, the biasing member 80 is provided with the reverse rotation restricting mechanism, and the biasing member 80 is also a reverse rotation restricting member. The reverse rotation restricting mechanism includes a meshing section 88 which is provided at a part facing the gear section 62 of the operational rotating roller 61 at a distal portion of the reverse rotation restricting member (which also serves as the biasing member) 80 and which meshes with the gear section 62, an elastically deformable section 86, and a mounting section 87 for mounting to the housing. In addition, the inner surface of the first housing 50a has a first projected part (bearing part) 59 and a second projected part 79. The first projected part 59 enters into the elastically deformable section 86 of the reverse rotation restricting member (biasing member) 80, and has an outer surface shape corresponding to the inner surface shape of the elastically deformable section 86. Specifically, the inner surface shape of the elastically deformable section 86 is arcuate, and the first projected part 59 has a cylindrical shape corresponding to the arcuate shape. The mounting section 87 of the reverse rotation restricting member (biasing member) 80 has a shape and size which permits the mounting section 87 to be mounted between the first projected part 59 and the second projected part 79 of the first housing 50a. In addition, the reverse rotation restricting member (biasing member) 80 has its mounting section 87 mounted between the first projected part 59 and the second projected part 79 of the first housing 50a, thereby being mounted in a non-turnable manner (i.e., the mounting section 87 is fixed against rotation and not rotatable), and biases the operational rotating roller 61 toward the opening section 58 by an elastic force of the elastically deformable section 86. The mounting section 87 of the reverse rotation restricting member (biasing member) 80 is restricted with respect to movement toward side surfaces by a disk-shaped projected part 13a provided on the collar member 12.

In addition, as above-mentioned, the roller 61 can be rotated by pressing it. Though the roller 61 can be rotated in the direction of the arrow in FIG. 18 (in the direction for winding up the pulling wires), an attempt to rotate the roller 61 in the reverse direction results in one tooth part of the gear section 62 engaging the meshing section 88 of the reverse rotation restricting member (biasing member) 80, whereby the attempted rotation is inhibited or prevented. By this, rotation of the roller in the reverse direction to the pulling wire winding-up direction of the pulling wire winding-up function is restricted. In this operating section 10, as shown in FIG. 19, the reverse rotation restricting member (biasing member) 80 is disposed between the inner surface of the first housing 50a and a side surface of the rotating roller 61. Therefore, movement of the reverse rotation restricting member (biasing member) 80 in lateral directions (horizontal directions) is restricted by the inner surface of the first housing 50a and the side surface of the rotating roller 61.

The outer diameter of the gear section 62 is smaller than the outer diameter of the rotating roller. The outside diameter of the gear section 62 is preferably about 10 to 60 mm, more preferably 15 to 50 mm. The number of teeth of the gear section 62 is preferably about 4 to 200, more preferably 4 to 70.

In addition, the collar member 12 of the operating section 10 has one end section borne by the pin 13, whereas the collar section 14 on the other end side contains the winding-up shaft section 63 so that an annular space exists between the outer surface of the winding-up shaft section 63 and the inner surface of the collar section 14. The annular space is not so large a space, and causes a narrower annular space to be formed between outer surfaces of the wires wound up.

A method of using the stent delivery system 1 according disclosed here will now be described.

As preparation for use, priming is conducted. As shown in FIG. 10, the cap member 47 is attached to the distal end member 25, to close the distal opening 25a. In this condition, a syringe filled with physiological saline is attached to the opening 23 of the fixing tube 8. Then, a plunger of the syringe is pressed, to inject the physiological saline into the distal-side tube 2. The injection of the physiological saline results in that, as shown in FIG. 10, the distal-side priming slit 45 and the proximal-side priming slit 46 are opened, and the physiological saline flows into the space formed in the inside of the distal-side tube and on the outside of the distal-side tube, in the stent delivery system, whereby priming is achieved. Then, the cap member 47 attached to the distal end member 25 is detached. The priming operation may be conducted by a method in which the opening 23 of the fixing tube 8 is sealed with a seal member or the like and the syringe filled with the physiological saline is attached to the distal end member 25.

Next, the terminal end of a guide wire which in many cases has already been set indwelling in a living body is inserted into the opening section 25a of the distal end member of the stent delivery system 1 for which priming has been finished, and the guide wire is led out via the opening 23. Subsequently, the stent delivery system 1 is inserted into a guiding catheter inserted in the living body, the stent delivery system 1 is pushed forward along the guide wire, and the stent containing part of the stent containing tubular member 5 is positioned in a target stenosed part.

Next, the operational rotating roller 61 of the operating section 10 is pressed by the user, and thereafter the roller is rotated in the direction of arrow in FIG. 18. This causes the pulling wires 6 to be wound up onto the outer peripheral surface of the winding-up shaft 63, and the stent containing tubular member 5 and the slide tube 7 are moved along the axial direction toward the proximal side (in the proximal direction). In this instance, the rear end face of the stent 3 abuts on, and is locked by, the distal end face of the stent proximal end lock section 22 of the distal-side tube 2. Therefore, upon movement of the stent containing tubular member 5, the stent 3 is released via the distal opening of the stent containing tubular member 5. By this release, as shown in FIG. 11, the stent 3 self-expands to dilate the stenosed part, and is indwelled or placed in the stenosed part.

The detailed description above describes features and aspects of embodiments, disclosed by way of example, of a stent delivery system and method of using (e.g., priming) a stent delivery system. The invention is not limited, however, to the precise embodiments and variations described and illustrated. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent delivery system comprising:
   a distal-side tube possessing a guide wire lumen;
   a proximal-side tube;
   a fixing tube fixed to a proximal portion of the distal-side tube and fixed to a distal portion of the proximal-side tube so as not to close a rear end opening of the distal-side tube;
   a stent containing tubular member enclosing a distal portion of the distal-side tube and slidable toward the proximal portion of the distal-side tube;
   at least one pulling wire extending inside the proximal-side tube, the at least one pulling wire having one end section fixed to the stent containing tubular member so that a proximal direction pulling force applied to the at least one pulling wire moves the stent containing tubular member in the proximal direction toward the proximal-side tube;
   a cylindrically-shaped stent located in the stent containing tubular member, the stent being located in the stent containing tubular member in a compressed state in which the stent is compressed inwardly toward a central axis of the stent, the stent being expandable outwardly when released to outside the stent containing tubular member;
   a stent proximal end lock section located on a distal side of the distal-side tube and abutting on a proximal end of the stent contained in the stent containing tubular member to restrict movement of the stent in the proximal direction;
   a plurality of axially spaced apart distal-side priming slits passing through a side wall of the distal-side tube in proximity to the stent proximal end lock section;
   a plurality of axially spaced apart proximal-side priming slits passing through the side wall of the distal-side tube on a proximal side of the distal-side tube; and
   the plurality of axially spaced apart distal-side priming slits and the plurality of axially spaced apart proximal-side priming slits having a first configuration and a second configuration, a width of the plurality of axially spaced apart distal-side priming slits and a width of the plurality of axially spaced apart proximal-side priming slits being greater in the second configuration than in the first configuration;
   the plurality of axially spaced apart distal-side priming slits and the plurality of axially spaced apart proximal-side priming slits configured to be opened and to thereby obtain the second configuration by injecting a liquid into the guide wire lumen of the distal-side tube, with a distal opening or a rear end opening of the guide wire lumen closed, such that, in the second configuration, the liquid passes through both the plurality of axially spaced apart distal-side priming slits and the plurality of axially spaced apart proximal-side priming slits;
   wherein an axial distance between a proximal-most distal-side priming slit and a distal-most proximal-side priming slit is greater than a distance between axially adjacent distal-side priming slits and greater than a distance between axially adjacent proximal-side priming slits and the axial distance between the proximal-most distal-side priming slit and the distal-most proximal-side priming slit is devoid of priming slits; and
   wherein at least some of the plurality of proximal-side priming slits are on a portion of the side wall of the distal-side tube disposed within a lumen of the fixing tube.

2. The stent delivery system according to claim 1, wherein at least one of the distal-side priming slits is located on a proximal side of the stent proximal end lock section.

3. The stent delivery system according to claim 1, wherein the plurality of distal-side priming slits and/or the plurality of proximal-side priming slits are parallel to a center axis of the distal-side tube.

4. The stent delivery system according to claim 1, wherein the distal-side tube includes a reinforcement layer extending over at least a part of the distal-side tube, and the plurality of distal-side priming slits and/or the plurality of proximal-side priming slits pass through the side wall of the distal-side tube at a location at which the reinforcement layer is located.

5. The stent delivery system according to claim 1, further comprising a slide tube disposed proximate to a proximal end of the stent containing tubular member, a distal end portion of the fixing tube axially overlapping a proximal end portion of slide tube, and the slide tube being movable in the proximal direction relative to the fixing tube together with the stent containing tubular member by pulling of the pulling wire, wherein the slide tube is not fixed to the stent containing tubular member.

6. The stent delivery system according to claim 5, wherein the slide tube includes a slide tube body and a distal-side tubular member, the distal-side tubular member being fixed to a distal portion of the slide tube body and covering a distal end of the slide tube body, the distal-side tubular member extending distally beyond the distal end of the slide tube body, and the distal-side tubular member being an integrally formed tubular body having a reduced diameter section located between the distal end of the distal-side tubular member end and the proximal end of the distal-side tubular member, the reduced diameter section possessing a reduced inside diameter relative to the inner diameter of portions of the distal-side tubular member on axially opposite sides of the reduced diameter section.

7. The stent delivery system according to claim 6, further comprising a ring-shaped member contained between the distal end of the slide tube body and the reduced diameter section of the distal-side tubular member, and the pulling wire is fixed to the ring-shaped member.

8. The stent delivery system according to claim 7, wherein the ring-shaped member is not fixed to either the slide tube body or the distal-side tubular member, and is turnably contained between the distal end of the slide tube body and the reduced diameter section of the distal-side tubular member.

9. The stent delivery system according to claim 5, further comprising a slide tube lock section provided in the fixing tube, at least some of the plurality of proximal-side priming slits being provided in the side wall of the distal-side tube at a location distal to the slide tube lock section.

10. The stent delivery system according to claim 1, further comprising an operating section located at a proximal portion of the proximal-side tube, the operating section comprising a pulling wire winding-up mechanism for winding up the pulling wire so as to move the stent containing tubular member in the proximal direction, the at least one pulling wire being connected to the pulling wire winding-up mechanism.

11. The stent delivery system according to claim 1, wherein an axial distance between a proximal-most proximal-side priming slit and the rear end opening of the distal side tube is greater than an axial distance between the proximal-most proximal-side priming slit and a distal end opening of the distal side tube.

12. A stent delivery system comprising:
a distal-side tube possessing a guide wire lumen to receive a guide wire, the guide wire lumen being surrounded by a side wall of the distal-side tube, the guide wire lumen extending from an open distal end to an open proximal end so that a guide wire received in the guide wire lumen passes through the open distal end of the guide wire lumen and passes through the open proximal end of the guide wire lumen;
a proximal-side tube;
a fixing tube positioned axially between the distal-side tube and the proximal-side tube;
a stent containing tubular member, a distal portion of the distal-side tube passing through the stent containing tubular member so that the distal-side tube and the stent containing tubular member axially overlap one another with an annular space between an inner surface of the stent containing tubular member and an outer surface of the distal-side tube, the stent containing tubular member being axially movable in a proximal direction relative to the distal-side tube;
at least one pulling wire positioned in the proximal-side tube and possessing an end fixed to the stent containing tubular member so that a pulling force applied to the at least one pulling wire in the proximal direction moves the stent containing tubular member in the proximal direction;
a cylindrically-shaped stent located in the annular space between the inner surface of the stent containing tubular member and the outer surface of the distal-side tube, the stent being compressed inwardly while in the annular space and being automatically expandable outwardly when released to outside the annular space;
a stent proximal end lock section fixed to the distal-side tube, the stent proximal end lock section being positioned axially between a proximal end of the stent and a proximal-most end of the stent containing tubular member to restrict movement of the stent in the proximal direction;
at least two distal-side priming slits and at least two proximal-side priming slits passing through the side wall of the distal-side tube, the at least two distal-side priming slits and the at least two proximal-side priming slits having a first configuration and a second configuration, a width of the at least two distal-side priming slits and a width of the at least two proximal-side priming slits being greater in the second configuration than in the first configuration, the at least two distal-side priming slits and the at least two proximal-side priming slits configured to be opened and to thereby obtain the second configuration upon injecting a liquid into the guide wire lumen while the open distal end or the open proximal end is closed, such that the liquid passes through both the at least two distal-side priming slits and the at least two proximal-side priming slits, the at least two distal-side priming slits and the at least two proximal-side priming slits being positioned between a proximal end of the stent containing tubular member and a distal end of the stent containing tubular member;
the at least two distal-side priming slits and the at least two proximal-side priming slits passing through the side wall of the distal-side tube at a location between a distal end of the stent containing tubular member and a proximal end of the stent containing tubular member; and
the at least two proximal-side priming slits disposed on a portion of the side wall of the distal-side tube located within a lumen of the fixing tube;
wherein an axial distance between a proximal-most one of the at least two distal-side priming slits and a distal-most one of the at least two proximal-side priming slits is greater than a distance between axially adjacent distal-side priming slits and greater than a distance between axially adjacent proximal-side priming slits and the axial distance between the proximal-most one of the at least two distal-side priming slits and the distal-most one of the at least two proximal-side priming slits is devoid of any priming slits.

13. The stent delivery system according to claim 12, wherein the at least two distal-side priming slits comprise a plurality of axially spaced apart distal-side priming slits and the at least two proximal-side priming slits comprise a plurality of axially spaced apart proximal-side priming slits, the plurality of distal-side priming slits and the plurality of proximal-side priming slits passing through the side wall of the distal-side tube at a location between the distal end of the stent containing tubular member and the proximal end of the stent containing tubular member.

14. The stent delivery system according to claim 12, wherein the at least two distal-side priming slits comprise a plurality of axially spaced apart distal-side priming slits passing through the side wall of the distal-side tube, the plurality of distal-side priming slits axially overlapping the stent proximal end lock section so that at least one of the distal-side priming slits is positioned distally of the stent proximal end lock section and at least one of the distal-side priming slits is positioned proximally of the stent proximal end lock section.

15. The stent delivery system according to claim 12, wherein the at least two distal-side priming slits comprise a plurality of axially spaced apart distal-side priming slits passing through the side wall of the distal-side tube and the at least two proximal-side priming slits comprise a plurality of axially spaced apart proximal-side priming slits passing through the side wall of the distal-side tube, the distal-side priming slits passing through the side wall of the distal-side tube at a location between the distal end of the stent containing tubular member and the proximal end of the stent containing tubular member, the proximal-side priming slits being located proximal of the distal-side priming slits and being positioned between a proximal end of the fixing tube and a distal end of the fixing tube.

16. The stent delivery system according to claim 12, wherein the fixing tube is fixed to a proximal portion of the distal-side tube and is fixed to a distal portion of the proximal-side tube.

17. The stent delivery system according to claim 12, further comprising a slide tube possessing a distal end portion axially overlapping a proximal end portion of the stent containing tubular member, the slide tube possessing a proximal end portion axially overlapping a distal end portion of the fixing tube, wherein the slide tube is not fixed to the stent containing tubular member, the slide tube including a reduced diameter section possessing a reduced inside diameter relative to the inner diameter of portions of the slide tube on axially opposite sides of the reduced diameter section, and further comprising a ring-shaped member to which the at least one pulling wire is fixed, the ring-shaped member being positioned proximally of the reduced diameter section.

18. The stent delivery system according to claim 17, further comprising a slide tube lock section provided in the fixing tube, at least two proximal-side priming slits being provided in the side wall of the distal-side tube at a location distal to the slide tube lock section.

\* \* \* \* \*